United States Patent [19]
Sato

[11] Patent Number: 6,067,706
[45] Date of Patent: May 30, 2000

[54] CLIP DRIVER

[76] Inventor: Hisao Sato, Fujimidai Mansion 2002, 29-10, Nukui 1-chome, Nerima-ku, Tokyo, Japan

[21] Appl. No.: 09/203,344

[22] Filed: Dec. 2, 1998

[30] Foreign Application Priority Data

Sep. 22, 1998 [JP] Japan .................................. 10-306276

[51] Int. Cl.[7] .............................. B23Q 7/10; B42B 5/00; B23P 11/00
[52] U.S. Cl. ............................ 29/809; 29/811.2; 29/814; 29/243.56; 412/28; 412/33
[58] Field of Search .................... 29/811.2, 814, 29/809, 243.56; 412/28, 33

[56] References Cited

U.S. PATENT DOCUMENTS

| | | | |
|---|---|---|---|
| 4,353,157 | 10/1982 | Sato | 29/243.56 |
| 4,996,755 | 3/1991 | Sato | 29/243.56 |
| 5,119,553 | 6/1992 | Sato | 29/243.56 |
| 5,136,768 | 8/1992 | Sato | 29/243.56 |
| 5,152,423 | 10/1992 | Tseng | 29/243.56 |
| 5,890,642 | 4/1999 | Sato | 29/243.56 |

FOREIGN PATENT DOCUMENTS 6-15994  1/1994  Japan .

*Primary Examiner*—P. W. Echols
*Attorney, Agent, or Firm*—Kanesaka & Takeuchi

[57] ABSTRACT

A clip driver is used for driving elastic clips each having a back portion, and abutment portions for clipping edge portions of sheet-members between the opposite ends of the abutment portions. The clip driver includes a casing body for accommodating the clips and including a sheet-member insertion inlet formed at a front end, a clip insertion inlet formed at a rear end, a longitudinally extending opening formed in a front end upper surface, a clip path formed so as to extend from the sheet-member insertion inlet to the clip insertion inlet, and clip stopper portions for engagement with the clips so as to allow the clips to advance but prevent the clips from retreating; clip opening springs disposed in the vicinity of the sheet-member insertion inlet for opening a nip between the abutment portions of the frontmost clip; an operation knob longitudinally movably fitted into the opening for feeding the frontmost clip in the clip path toward the sheet-member insertion inlet over the clip opening springs by means of the front end of the operation knob; a feed member movable together with the operation knob and having feed protrusions which make a second and following clips advance simultaneously when the feed member advances, while the feed member can retreat without making the advanced clips retreat by the feed protrusions; and an elastic member always elastically biasing the operation knob and the feed member toward the rear end of the casing body.

10 Claims, 14 Drawing Sheets

FIG. 3a
FIG. 3b
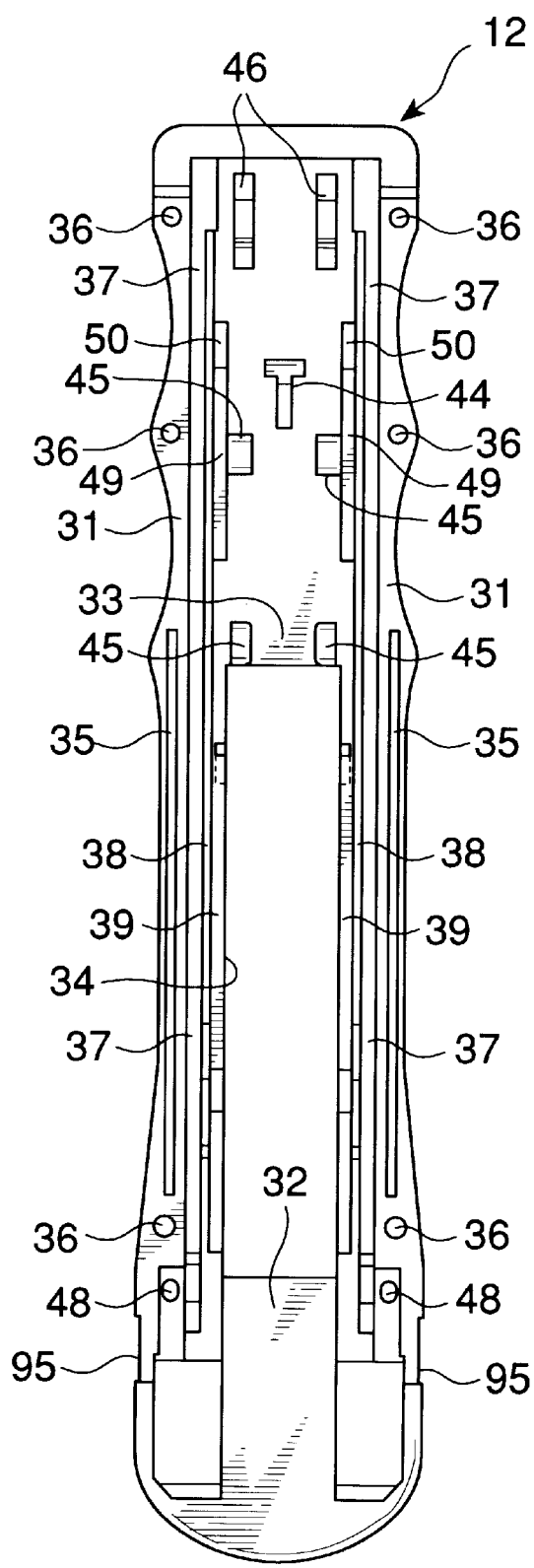
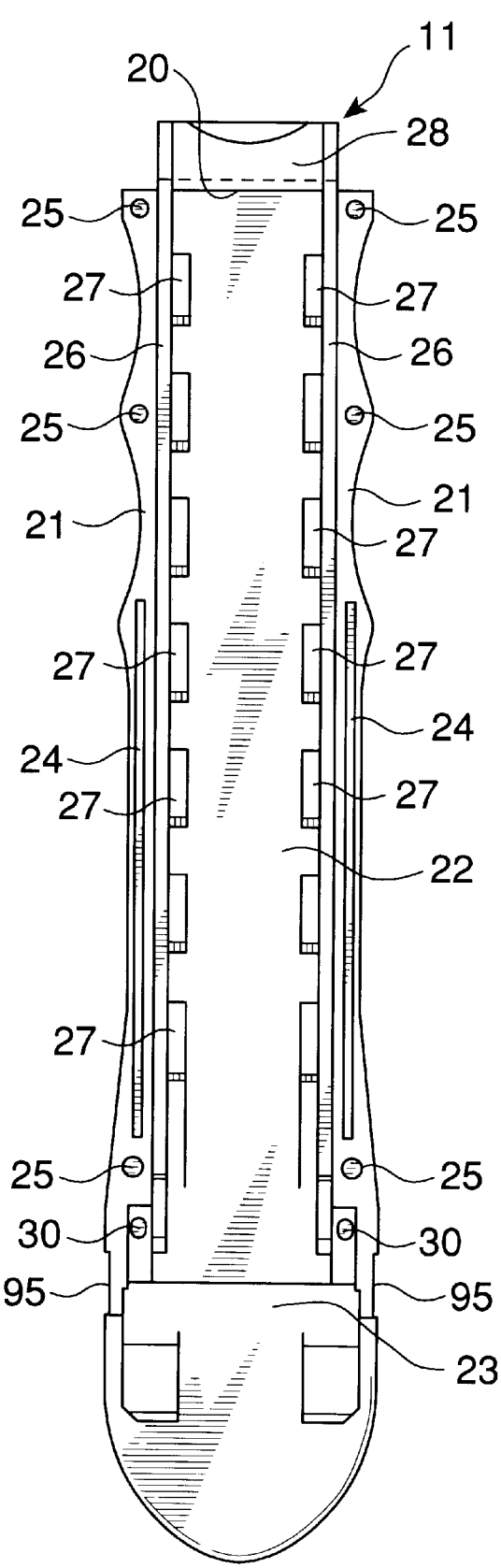

CLIP DRIVER

BACKGROUND OF THE INVENTION

1. Field of the Invention

The present invention relates to a clip driver for binding edges of sheets of paper such as documents or the like by using a clip, and particularly relates to a clip driver in which a plurality of clips each being formed of a sheet of elastic plate-like member bent to have abutment portions on its longitudinally opposite ends is accommodated and successively sent to a position in which the abutment portions are opened so as to grasp the sheets of paper therebetween.

2. Description of the Related Art

In JP-Y-58-4698, the Applicant of this application has proposed not only a clip which is formed of a sheet of elastic plate-like member so as to have a back portion formed at the longitudinal center of the plate-like member and abutment portions formed so as to be continued to this back portion so that their front ends abut against each other, but also a clip driver for opening the abutment portions of such a clip so as to make the clip grasp sheets of paper such as documents between the abutment portions. This clip driver is constituted by: a driver body having a paper insertion inlet formed at its front end for inserting end portions of sheets of paper to be clipped, a clip insertion inlet formed at its rear end, and a storage portion formed in its inside for storing clips; clip opening springs provided near the paper insertion inlet in the driver body so as to be inserted between the abutment portions of a clip to thereby open the abutment portions against the elasticity of the clip; and a lever removably inserted into the storage portion from the rear end of the storage portion so as to engage with a back portion of a clip to thereby push the clip toward the paper insertion inlet. When sheets of paper are to be clipped, the sheets of paper are inserted into the paper insertion inlet, and a clip is moved toward the paper insertion inlet by the lever. If the clip is further moved, the clip opening springs are inserted into the opening between the abutment portions of the clip. The clip is further moved toward the paper insertion inlet while opening the abutment portions to reach a position where the sheets of paper placed in the paper insertion inlet are held between the abutment portions of the clip. If the lever is further moved forward, the clip is removed from the clip opening springs, so that the clip can be ejected from the paper insertion inlet in a state where the clip grasps the sheets of paper between the abutment portions.

In the clip driver proposed in the above-mentioned JP-Y-58-4698, there was a defect that it was impossible to charge a plurality of clips in the storage portion because one clip is pushed out by the front end of the lever. Therefore, in U.S. Pat. No. 4,353,157, the inventor of this application proposed a clip driver in which a knob was provided on the upper surface of a storage portion of a driver body so that the knob could slide in the front/rear or longitudinal direction and the front end portion of the knob could move down. In the clip driver, if this knob was advanced while being pushed-down, a clip was pushed out to the position of clip opening springs. Further, a plurality of clips could be charged in a storage portion. After the first clip was pushed out, the knob was moved back to abut against the back portion of the next clip, so that the next clip could be moved to the portion of the clip opening springs. In this clip driver proposed in U.S. Pat. No. 4,353,157, it was necessary to move back the knob by a finger whenever a new clip was to be positioned to the portion of the clip opening springs, so that there was a problem that the operation was troublesome, although a plurality of clips could be stored so that a plurality of sets of sheets of paper could be clipped continuously.

Therefore, in U.S. Pat. No. 4,996,755, the inventor of this application further proposed a clip driver in which a knob protrusion was projected on the upper surface of the front end of a knob, while the knob was always kept backward and upward by a spring. When sheets of paper were to be clipped by this clip driver, the knob was pushed down against the elastic force of tie spring and moved forward to thereby push out a first clip. Since the knob was moved up and back when the thumb handling the knob was separated from the knob, the knob could move back, without being disturbed by the next clip, so as to push out the next clip.

According to the clip driver in U.S. Pat. No. 4,996,755, it became possible to clip end portions of sheets of paper only by the operation to move the knob forward, and it became possible to clip sets of sheets of paper continuously. However, to sent the next clip, it was necessary to release the knob from pressure, and then lower the front end side of the clip driver so as to make the clip slide and move toward the front end by its own weight. This led to a disadvantage that it was impossible to perform clipping continuously.

In JP-A-6-15994, on the other hand, a clip driver which can perform clipping continuously is proposed. In this clip driver, a notch portion extending in the front/rear or longitudinal direction is provided in the upper surface of a casing body, a clip insertion inlet is provided in the rear side of the notch portion for inserting a clip, and a cover covering this notch portion is provided so that the rear end of the cover is rotatable at the rear end of the casing body. Such a knob as mentioned above is provided in the cover so as to be movable in the front/rear or longitudinal direction. A clip pushing member is inserted into the casing body so as to push a clip located at the rearmost position toward the front end. This clip pushing member and the knob are connected through a coil spring. With this configuration, the clip pushing member is urged by the coil spring so as to be positioned at the rear of the clip insertion inlet when the cover is opened. Consequently, a clip at the rearmost position can be pushed toward the front end whenever the cover is closed so that clips inserted from the clip insertion inlet can be fed out continuously by this pushing force.

However, in the clip driver in JP-A-6-15994, the casing body is required to have a length which is equal to the sum of the length of the clip pushing member and the total length of a maximum number of the clips to be accommodated in the casing body. It is therefore inevitable that the clip driver is made longer than a conventional one. In addition, it is the weakest point of this clip driver that it is difficult to attach the clips because it is necessary to open the cover against the expansion/contraction force of the spring in order to fill up the clips, and because the insertion hole is narrow enough to prevent the clips from coming out therefrom.

SUMMARY OF THE INVENTION

It is therefore an object of the present invention to solve the foregoing problems.

It is another object of the present invention to provide a clip driver in which a plurality of clips can be filled up easily from the rear end of the clip driver, so that continuous paper clipping can be performed while the clip driver has a length substantially equal to that of a conventional one.

In order to achieve the above objects, according to an aspect of the present invention, provided is a clip driver for driving a plurality of clips one by one, each of the clips being formed from an elastic plate-like body having a back portion and abutment portions, the abutment portions being formed by bending the elastic plate-like body in the same direction at longitudinally opposite ends of the back portion so that opposite ends of the abutment portions abut against each other elastically whereby the clip can hold edge portions of sheet-like members to be clipped between the opposite ends of the abutment portions, the clip driver comprising: a casing body for accommodating the plurality of clips, the casing body including a sheet-like member insertion inlet formed at a front end of the casing body for inserting the sheet-like members to be clipped, a clip insertion inlet formed at a rear end of the casing body for inserting the clips one by one, an opening formed in a front end upper surface of the casing body so as to extend in a longitudinal direction of the casing body, a clip path formed in the casing body so as to extend from the sheet-like member insertion inlet to the clip insertion inlet, and clip stopper means for engagement with the clips so as to allow the clips to advance but prevent the clips from retreating; clip opening springs disposed in the casing body in the vicinity of the sheet-like member insertion inlet of the casing body for opening a nip between the abutment portions of the clip; an operation knob fitted into the opening so as to be movable in the longitudinal direction of the casing body for feeding a frontmost one of the clips in the clip path toward the sheet-like member insertion inlet over the clip opening springs by means of a front end of the operation knob; a feed member which is movable together with movement of the operation knob in the longitudinal direction of the casing body, the feed member having a plurality of feed protrusions which make second and following ones of the clips advance simultaneously when the feed member advances, while the feed member can retreat without making the advanced clips retreat by the feed protrusions; and an elastic means for always elastically biasing the operation knob and the feed member toward the rear end of the casing body.

Preferably, the clip driver further comprises a connection member for connecting the operation knob and the feed member to each other so that the feed member advances after only the operation knob advances by a predetermined distance to feed the frontmost clip forward.

Preferably, the clip driver further comprises a connection member connected to the feed member in such a manner that one end of the connection member is connected to the operation knob and the other end of the connection member is connected to the feed member in a manner so that the other end is loosely fitted into a long hole which is formed in the feed member so as to extend in the longitudinal direction of the feed member, whereby the feed member advances after only the operation knob advances by a predetermined distance to feed the frontmost clip forward.

Preferably, in the above clip driver, the casing body includes restriction/guide protrusions which are formed so as to keep the feed member in a first position when the feed member advances and in a second position higher than the first position when the feed member retreats, whereby a rear end of the feed member is located in the upper portion of the clip insertion inlet so that, when a clip is to be inserted into the clip insertion inlet, the feed member is moved forward by the clip to be inserted so as to allow insertion of the clip, while the thus inserted clip is prevented from falling out of the clip insertion inlet by the rear end of the feed member.

Preferably, in the above clip driver, the casing body includes restriction/guide protrusions which are formed at rear portions inside the casing body for keeping the feed member in a first position when the feed member advances and in a second position higher than the first position when the feed members retreats, the restriction/guide protrusions being disposed at an interval in the longitudinal direction on each of widthwise opposite side portions of the casing body, and the feed member includes engagement protrusions which are formed at an interval in the longitudinal direction on each of widthwise opposite side surfaces in front and rear end portions of the feed member so that when the feed member is made to retreat, the feed member retreats in a state that the engagement protrusions are mounted on the restriction/guide protrusions.

Preferably, in the above clip driver, the casing body includes restriction/guide protrusions which are formed at rear portions inside the casing body so as to be disposed at an interval in the longitudinal direction on each of widthwise opposite side portions of the casing body; in each pair of the restriction/guide protrusions disposed at front and rear positions in the longitudinal direction, each of the restriction/guide protrusions located at the rear position is constituted by a horizontal portion extending substantially horizontally from a front end to a rear end thereof and a slanting portion extending upward from the rear end of the horizontal portion toward the rear of the casing body; the casing body further includes ribs which are formed on widthwise opposite side portions of the opening of the casing body so as to slightly project toward the opening and extend longitudinally in a height substantially identical with the height of the horizontal portions of the rear-side restriction/guide protrusions; and the feed member includes engagement protrusions which are disposed at an interval on longitudinally front and rear ends of each of widthwise opposite sides of the feed member so that, when the feed member is made to retreat, the feed member retreats in a state that the engagement protrusions are mounted on the restriction/guide protrusions, and the feed member further includes elastic members formed on widthwise opposite sides at a rear end lower portion of the feed member so that the elastic members engage with lower surfaces of the rear-side restriction/guide protrusions, whereby when the feed member advances, the front-side engagement protrusions of the feed member are mounted on the ribs while the rear-side engagement protrusions and the elastic members sandwich the horizontal portions therebetween so that the feed member can advance substantially horizontally.

Preferably, in the above clip driver, each of the clip stopper means and the feed protrusions has a rear end constituted by a slanting surface and a front end constituted by a substantially vertical surface.

Preferably, the above clip driver further comprises a connection member one end of which is longitudinally movably connected to the feed member while the other end of which is rotatably connected to the operation knob, so that the feed member advances after only the operation knob advances by a predetermined distance to feed the frontmost clip forward.

Preferably, in the above clip driver, the clip stopper means includes a plurality of clip stopper protrusions formed at intervals each of which is substantially equal to a length of each clip from the back portion to the forward end of the abutment portions.

Preferably, in the above clip driver, each of the elastic members is constituted by an elastic arm having an end fixed on a side lower surface of the feed member and being extended upward, and a projected pin formed at a free end of the elastic arm so as to be able to slidably contact with the lower surface of the rear-side restriction/guide protrusion.

BRIEF DESCRIPTION OF THE DRAWINGS

FIG. 3a is a plan view illustrating an upper casing of the casing portion in the embodiment;

FIG. 3b is a plan view illustrating a lower casing of the same casing portion;

DETAILED DESCRIPTION OF THE PREFERRED EMBODIMENT

Figure 16:
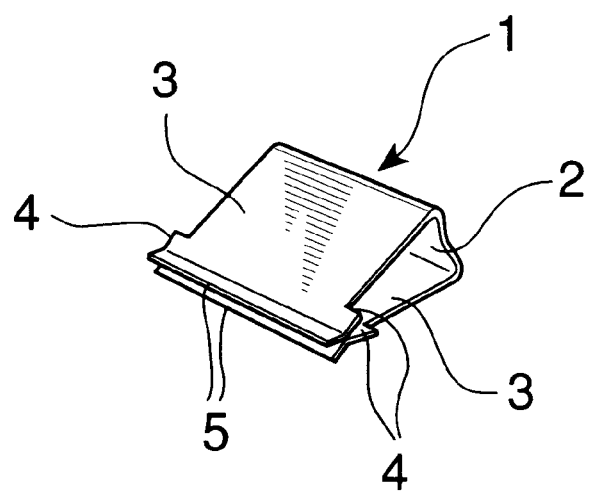
FIG. 16 is a perspective view illustrating an example of a clip to be used in the embodiment.

An embodiment of the clip driver according to the present invention will be described below with reference to the accompanying drawings. First, an example of known clip to be used in this clip driver will be described with reference to FIG. 16 which is a perspective view illustrating such a clip. A clip 1 is formed by bending a band-like elastic plate-like body consisting of a metal plate or a synthetic resin plate. The clip 1 is constituted by: a back portion 2 which is formed at the longitudinally central portion of the plate-like body so as to have a length substantially equal to the maximum clipping thickness and so as to be curved inward; a pair of abutment portions 3 formed by bending the plate-like body at the longitudinally opposite end portions of the back portion 2 in the same direction so as to have extremities elastically abutting against each other; and a pair of lug portions 4 provided respectively on the edge portions of each of the abutment portions 3 so as to project in the direction perpendicular to the front/rear or longitudinal direction (hereinafter, the length in this direction perpendicular to the front/rear or longitudinal direction will be referred to as "width"). In the free ends of the respective abutment portions 3 including these lug portions 4, guide portions 5 bent outward respectively are formed so as to be opened easily.

Next, a clip driver for clipping sheets of paper with such a clip 1 will be described with reference to FIGS. 1 to 15.

A clip driver 10 is constituted mainly by: a substantially rectangular lower casing 11 in which a plurality of clips 1 can be loaded on its upper surface in a state where the clips 1 are arranged in a row; an upper casing 12 attached on the lower casing 11 so as to cover the lower casing 11; an operation knob 13 for feeding a frontmost one of the clips 1; a feed member 14 for engaging with a second clip 1 and the followings to feed those clips 1 sequentially; a connection member 15 for connecting the operation knob 13 and the feed member 14 to each other; a spring 16 for elastically biasing the operation knob 13 and the feed member 14 so that the operation knob 13 and the feed member 14 are moved back normally; and a pair of clip opening springs 17 for opening a space between the pairs of lug portions 4 of the clip 1. A casing body is constituted by the lower casing 11 and the upper casing 12. All the lower casing 11, the upper casing 12, the operation knob 13, the feed member 14 and the connection member 15 are formed of synthetic resin, while the spring 16 and the clip opening springs 17 are formed of metal. In the following description, "front end" means the end portion from which documents or the like are to be inserted, and which is shown in the left or lower side in the drawings; and "rear end" means the end portion from which clips are to be charged, and which is shown in the right or upper side in the drawings. In addition, "width" in the lower casing 11 or the upper casing 12 means the length perpendicular to the front/rear or longitudinal direction, and "moving direction" of the clips 1, the operation knob 13, the feed member 14 and so on means the direction of a movement from the rear end toward the front end.

Figure 1:
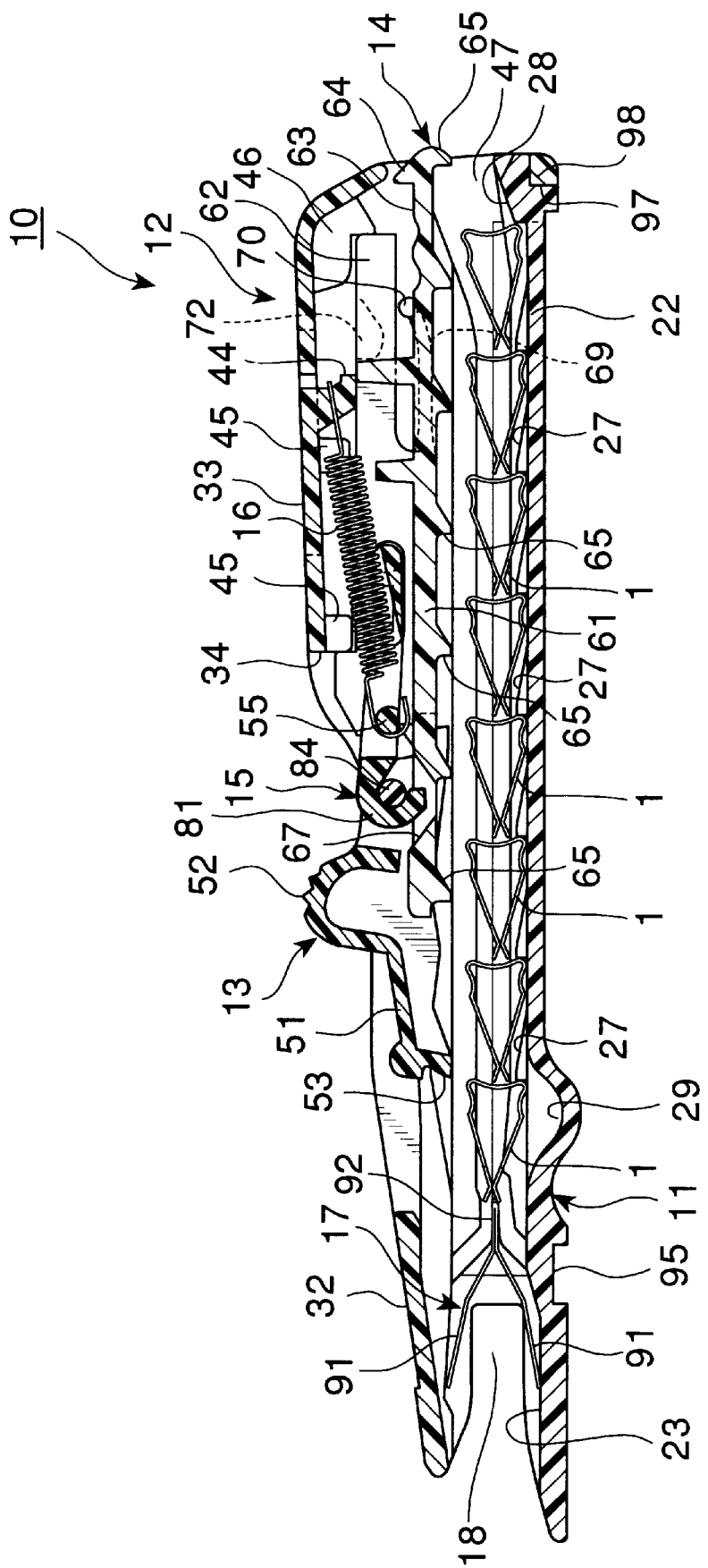
FIG. 1 is a longitudinally sectional side view illustrating an embodiment of the present invention together with clips.
Figure 2:
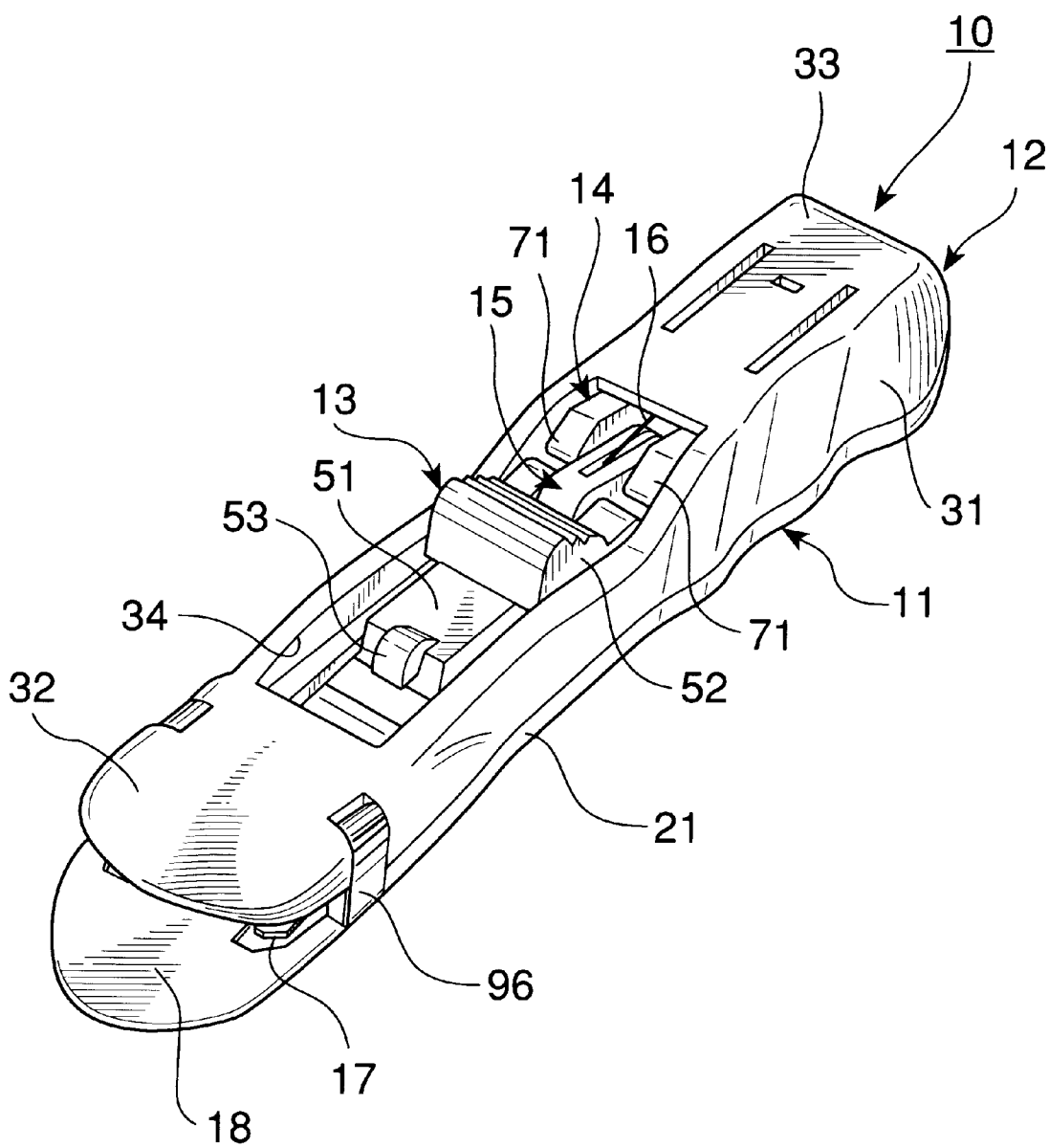
FIG. 2 is a perspective view illustrating the embodiment.
Figure 4:
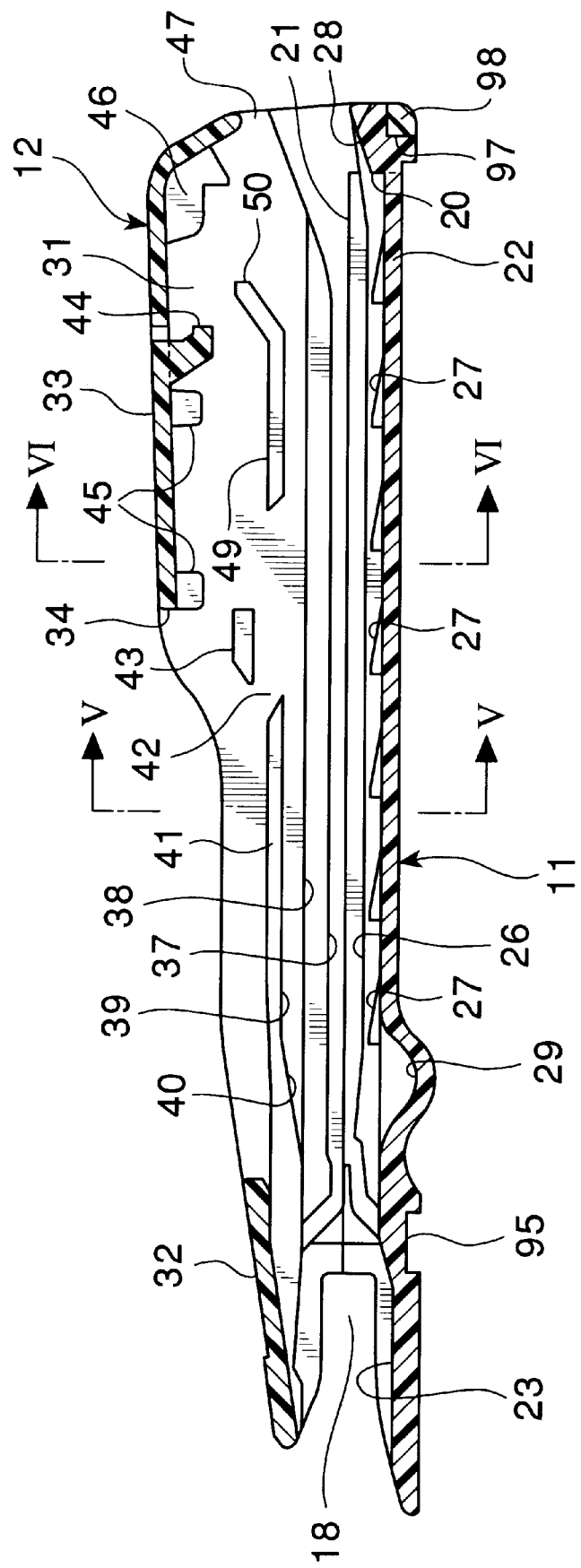
FIG. 4 is a longitudinally sectional side view illustrating only the casing portion in the embodiment, where both the upper and lower casings have been combined.

As shown in FIG. 3b and FIGS. 4 to 6, the lower casing 11 is constituted by a pair of lower side walls 21 and a bottom portion 22 disposed between these lower side walls 21 so that the lower casing 11 has a cross section substantially like a saucer. The width of the upper surface of the bottom portion 22 is selected to be substantially equal to the width of the abutment portions 3 of the clip 1. Consequently, the back portion 2 of the clip 1 and the lower corner portions of the abutment portions 3 of the clip 1 can pass through the lower casing 11. The front ends of both the lower side walls 21 terminate at positions a slightly rear side away from the front end portion of the bottom portion 22. A discharge lower surface 23 for discharging the clip 1 is formed in the bottom portion 22 in front of the front end portions of both the lower side walls 21. In the upper end surface of each lower side wall 21, an engagement protrusion 24 for engagement with the upper casing 12 and a plurality of positioning protrusions 25 are erected integrally therewith. In the inner surfaces of the lower side walls 21 opposite to each other, hook-like lower lug-guide grooves 26 are formed respectively, so that the pairs of lug portions 4 of the clip 1 can pass through the lower lug-guide grooves 26 respectively. As shown in FIG. 4, the front end portion of each of the lower lug-guide grooves 26 is formed so as to have a slight ascent and subsequently a descent stepwise down to the same level as the discharge lower surface 23.

Seven pairs of clip stopper protrusions 27 are formed at predetermined intervals in the bottom portion 22 of the lower casing 11. These pairs of clip stopper protrusions 27 contact with the lug-guide grooves 26 at their one side portions, and the clip stopper protrusions 27 are arranged widthwise two by two so as to be paired with each other. In each of the clip stopper protrusions 27, a substantially vertical surface is formed on the front end, and a gentle slope is formed on the rear end side so as to extend from the vertex of this vertical surface. Consequently, the clip 1 fed from the rear end side is fed to the front end side as if it climbs the gentle slopes of a pair of clip stopper protrusions 27. When the clip 1 has climbed over the pair of clip stopper protrusions 27, the back portion 2 of the clip 1 abuts against the vertical surfaces of the pair of clip stopper protrusions 27 conquered by the clip 1, so that the clip 1 is prevented from going back to the rear end side. The pitch of the respective pairs of clip stopper protrusions 27 is made so as to be a little longer than the length of the clip 1 from the back portion 2 to the front ends of the guide portions 5, so that the clip 1 can be disposed with this pitch. A slope 28 inclined obliquely upward from the front end side toward the rear end side is formed on the rear end portion of the bottom portion 22 of the lower casing 11 so that a clip 1 may fall into this slope 28. A step portion 20 descending substantially vertically is formed in the front end portion of this slope 28. A recess portion 29 is formed in the upper surface of the bottom portion 22 on the rear end side behind the rising portions of the front end portions of the lower lug-guide grooves 26 to thereby form an outward convex portion on the lower surface of the lower casing 11 so that a finger can be put on the convex portion. On the rear end opposite sides of the discharge lower surface 23 of the bottom portion 22, pin protrusions 30 for fixing the clip opening springs 17 are integrally erected.

The upper casing 12 is constituted by a pair of upper side walls 31, a front upper plate 32 disposed on the front end side between the upper side walls 31, and a rear upper plate 33 disposed on the rear end side and between the upper side walls 31, as shown in detail in FIG. 3a and FIGS. 4 to 6. An opening 34 to which the operation knob 13 is to be fitted loosely is formed between the front upper plate 32 and the rear upper plate 33 so that the operating knob 13 is movable in the front/rear or longitudinal direction. The respective upper side walls 31 are formed so as to be lowered toward the front end and raised from a portion of the opening 34 to the rear end, as shown in FIG. 4. In the lower end surfaces of the upper side walls 31, engagement grooves 35 and positioning holes 36 are formed so that the engagement protrusions 24 and the positioning protrusions 25 of the lower casing 11 can be inserted to those grooves 35 and holes 36 respectively when the upper casing 12 is combined with the lower casing 11. A paper insertion inlet 18 for inserting documents to be clipped thereto, binding the inserted documents with a clip, and extracting the clipped documents therefrom, is formed by the front upper plate 32 of this upper casing 12 and the discharge lower surface 23 of the lower casing 11.

In the opposite surfaces of the respective upper side walls 31, hook-like upper lug-guide grooves 37 are formed so as to extend from the rear end side to the front end side, so that guide grooves which allow the lug portions 4 of the clip 1 to pass are formed in cooperation with the lower lug-guide grooves 26 of the lower casing 11. The front end portions of the upper lug-guide grooves 37 is flat following a slight descent, and subsequently forms a slope inclined obliquely upward in the direction from the rear end side to the front end side. The front ends of the upper lug-guide grooves 37 terminate in the vicinity of the lower surface of the front upper plate 32. These front end portions of the upper lug-guide grooves 37 are disposed so as to project slightly toward the front end side from the front end portions of the lower lug-guide grooves 26. The rear end portions of the upper lug-guide grooves 37 are formed so that the distance between the rear end portions of the upper lug-guide grooves 37 and the rear end portions of the lower lug-guide grooves 26 increases gradually. Consequently, grooves passed by the lug portions 4 of the clip 1 are formed, from the rear end side to the front end side inside the casing body, in combination of the lower lug-guide grooves 26 of the lower casing 11 and the upper lug-guide grooves 37 of the upper casing 12.

Above the respective upper lug-guide grooves 37, upper clip-guide grooves 38 for allowing the back portion 2 of the clip 1 and the upper corner portions of the abutment portions 3 of the same to pass are formed as eaves for the upper lug-guide grooves 37 respectively. The respective front end portions of these upper clip-guide grooves 38 are located on the front end side of an opening 34, and the rear end portions of the same are located above the rearmost clip stopper protrusions 27. Consequently, grooves for allowing the back portion 2 and the abutment portions 3 of the clip 1 to pass are formed in combination of the upper surface of the bottom portion 22 of the lower casing 11 and the upper clip-guide grooves 38.

In the respective upper side walls 31 above the respective upper clip-guide grooves 38, base guide grooves 39 engaged movably by front engagement portions 54 and rear engagement portions 56 of the operation knob 13 which will be described later are further formed as eaves for the upper clip-guide grooves 38, respectively. The base guide grooves 39 are extending in the front/rear or longitudinal direction of the opening 34 while the length of each of the base guide grooves 39 is shorter than the longitudinal length of the opening 34. In the front end portion of each of the base guide grooves 39, a slope 40 is formed so that it is gradually descending toward the front end side from the vicinity above the clip stopper protrusion 27 standing in the front. The front end portions of the respective slopes 40 are disposed above the vicinity of the step-like descending portions of the corresponding lower lug-guide grooves 26 of the lower casing 11.

Above the base guide grooves 39 of the respective upper side walls 31, knob guide ribs 41 are formed respectively. The upper surfaces of the knob guide ribs 41 support the respective lower ends of engagement protrusions 57 of the operation knob 13 and front engagement protrusions 71 of the feed member 14, which will be described below. The bottom portions of the knob guide ribs 41 are projecting so as to form eaves for the base guide grooves 39, respectively. That is, the distance between the opposite end surfaces of the projecting end portions of the two knob guide ribs 41 is shorter than the distance between the base guide grooves 39 which are opposite-to each other thereunder to thereby prevent the operation knob 13 from coming off from the space between the knob guide ribs 41. On the other hand, this distance between the base guide grooves 39 is shorter than the distance between the upper clip-guide grooves 38 which are opposite to each other thereunder, so as to prevent the clip 1 from coming off from the space between the base guide grooves 39. The rear ends of the knob guide ribs 41 terminate in the front side of the rear end portion of the opening 34, and their end surfaces are inclined obliquely downward. In the respective upper side walls 31 at the rear of the knob guide ribs 41, restriction protrusions 43 are formed in one-degree higher positions respectively. The restriction protrusions 43 restrict the upper portion of an insertion inlet 42 for inserting the operation knob 13 or the feed member 14 in cooperation with the rear end portions of the knob guide ribs 41, while the front engagement protrusions 71 of the feed member 14 run on the upper surfaces of the restriction protrusions 43 when the feed member 14 goes back as will be described later. The front edge portions of the restriction protrusions 43 are inclined obliquely upward toward the rear end side.

In the substantially central portion of the lower surface of the rear upper plate 33, an engagement hook 44 for engagement with one end of the spring 16 is formed so as to hang down. In the lower surface of the rear upper plate 33 in front of this engagement hook 44, four hold protrusions 45 are formed so as to hang down at intervals in the front/rear or longitudinal direction and in the left/right direction. In the lower surface on the rear end side of the rear upper plate 33, a pair of engagement protrusions 46 are formed so as to hang down at a distance in the left/right direction. The hold protrusions 45 and the engagement protrusions 46 engage with the feed member 14 as will be described below. The rear end of the rear upper plate 33 hangs down, and the end portion thereof forms a slightly wide clip insertion inlet 47 for the clip 1 in combination with the slope 28 of the lower casing 11. Pin holes 48 to which the pin protrusions 30 of the lower casing 11 are to be inserted are formed in the lower surface on the rear end side of the front upper plate 32. The reference numerals 49 represent guide protrusions formed to project substantially horizontally at the rear of the respective upper side walls 31, and located between projected pins 70 and rear engagement protrusions 72 of the feed member 14, as will be described later. The guide protrusions 49 act to guide the feed member 14 so as to advance the second and following clips 1 surely when the feed member 14 goes ahead. The height and thickness of these guide protrusions 49 are substantially equal to those of the above-mentioned knob guide ribs. Ascending slopes 50 inclined upward toward the rear end side are formed on the rear end portions of the guide protrusions 49 respectively. The upper surfaces of the horizontal portions of these guide protrusions 49 are formed substantially on the same level as the upper surfaces of the knob guide ribs 41, while the lower surfaces of the horizontal portions are formed substantially on the same level as the upper surfaces of the base guide grooves 39. The rear edges of the ascending slopes 50 are formed substantially horizontally, and the height of their horizontal surfaces are formed substantially on the same level as the height of the restriction protrusions 43.

Next, the structure of the operation knob 13 will be described with reference to FIGS. 7 to 10. This operation knob 13 is constituted mainly by a base portion 51 having a sectional shape like an inverted gutter, extending in the direction of movement, and descending toward the front side on its front end portion, and a knob protrusion 52 integrally formed substantially at the center of this base portion 51. The width of the base portion 51 in the direction perpendicular to the direction of movement is a little shorter than the space between the opposite front ends of the knob guide ribs 41 of the rear casing 11. A push-out portion 53 and front engagement portions 54 are formed in the front end portion of the base portion 51. The push-out portion 53 is projecting downward from the front end of the base portion 51 so as to abut against the back portion 2 of the clip 1 located in the front. The front engagement portions 54 are projecting perpendicularly to the direction of movement from both sides of the front end of the base portion 51 so that the upper surfaces thereof can engage with the base guide grooves 39 movably. The rear end portion of the base portion 51 is cut out in its upper surface. Exposed from this cut-out portion, an engagement pin 55 and rear engagement portions 56, which will be described below, are formed in the rear end portion of the base portion 51. The engagement pin 55 is to engage with a hook portion 81 of the connection member 15, and the rear engagement portions 56 are projecting perpendicularly to the direction of movement from both sides of the rear end of the base portion 51 so that the upper surfaces thereof can engage with the base guide grooves 39 movably. The rear end surface of the base portion 51 is formed to be inclined toward the front end. The rear edge of the cut-out portion which is a rear end portion of the base portion 51 is made an end surface inclined obliquely upward toward the front.

The knob protrusion 52 is projecting up from the base portion 51, and its sectional shape in the direction of movement is substantially semi-circular. The width of the knob protrusion 52 in the direction perpendicular to the direction of movement is larger than the width of the base portion 51 in the same direction, and a little smaller than the width of the opening 34 of the upper casing 11. In the respective lower surfaces of the portions of the knob protrusion 52 projecting from the base portion 51, two engagement protrusions 57 are formed at a distance in the direction of movement. The lower ends of these engagement protrusions 57 are movably put in engagement with the upper surfaces of the knob guide ribs 41.

Next, the structure of the feed member 14 will be described with reference to FIG. 7 and FIGS. 11a–11c. The feed member 14 has a rectangular base portion 61 for engaging with the upper portions of the respective back portions 2 of the second and following clips 1, and side plate portions 62 formed so as to erect on the opposite sides of the base portion 61 at the substantially center portion. The distance or thickness between the outer surfaces of the opposite side plate portions 62 is designed to be shorter than the distance or space between the opposite end surfaces of the knob guide ribs 41 of the upper casing 12. The base portion 61 has an elastic portion 63 having a narrow and waved shape and extending to the rear side from a position slightly rear-sided from the longitudinally central portion of the base portion 61. An edge portion 64 having a width substantially equal to the distance between the outer surfaces of the opposite side plate portions 62 is formed at the rear end portion of the elastic portion 63.

Seven clip feed protrusions 65 are formed at predetermined intervals on the back surface of the base portion 61 from its front end portion to the edge portion 64. A substantially vertical surface is formed on the front side of each of these seven clip feed protrusions 65. The back portion 2 of the clip 1 is brought into contact with this vertical surface so that the clip 1 is prevented from going back toward the rear end during feeding of the clip. In addition, the rear Was end side of each of the respective feed protrusions 65 is formed to be a gentle slope so that the feed protrusion 65 can go back over the clip 1 when the feed member 14 goes back. The surface of the edge portion 64 is formed to be a slope 66 inclined obliquely upward from the rear end toward the front end. An inverted-trapezoidal opening 67 having an upper opening larger than a lower opening is provided on the front end side of the base portion 61. The upper surface of the front end portion of the base portion 61 extending from the front end of this opening 67 is made to be thicker or higher than the rear part of the upper surface of the base portion 61.

The front end of each of the side plate portions 62 is erected from the side edge of the base portion 61 integrally therewith, while the lower end on the rear end side is cut out by the notch portion 68 so that the lower edge is located above the upper surface of the base portion 61. Elastic arms 69 are formed in the notch portions 68 of the side plate portions 62 integrally therewith, respectively. The elastic arms 69 extend from the side plate portions 62 within the notch portions 68, and bend upward to the rear side, respectively. The front ends of the respective elastic arms 69 are disposed in the notch portions 68, respectively. Projected pins 70 projecting perpendicular to the direction of movement are formed at the front ends of the elastic arms 69. The front engagement protrusions 71 projecting perpendicularly to the direction of movement are formed on the front end upper side surfaces of the side plate portions 62 integrally therewith, respectively. In addition, rear engagement protrusions 72 are formed on the rear end side surfaces of the side plate portions 62 integrally therewith, respectively. The rear engagement protrusions 72 are projecting perpendicularly to the direction of movement in the same manner, but their projection length is shorter than that of the front engagement protrusions 71. The rear-end-side lower surfaces of these front engagement protrusions 71 and rear engagement protrusions 72 are made to be ascending slopes in the direction toward the rear side. In addition, long holes 73 extending in the direction of movement are made in the side surfaces of the front end portions of the side plate portions 62, respectively.

Figure 12:
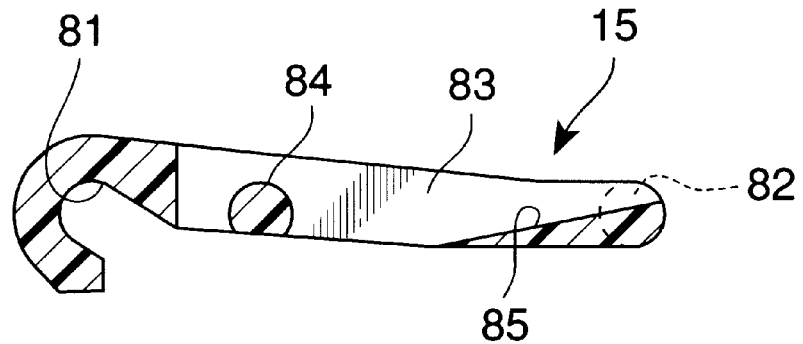
FIG. 12 is a longitudinally sectional view of the connection member in FIG. 7.
Figure 13:
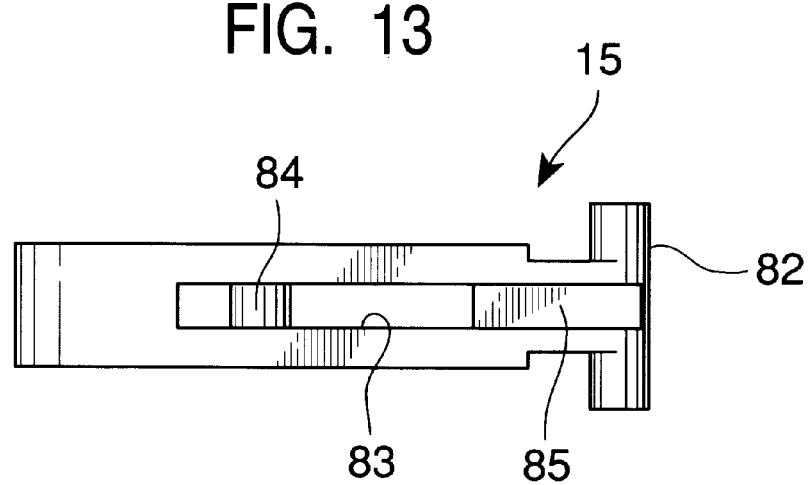
FIG. 13 is a plan view of the connection member in FIG. 7.
Figure 14:
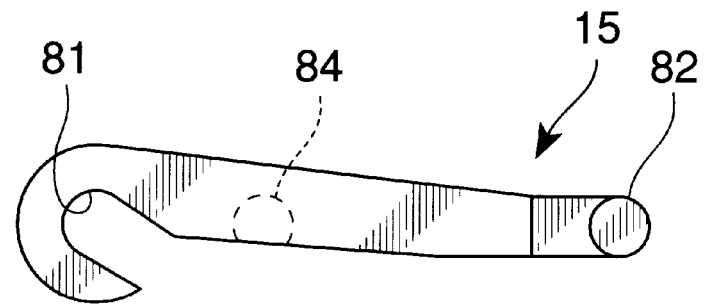
FIG. 14 is a side view of the connection member in FIG. 7.

In the connection member 15 for connecting the operation knob 13 and the feed member 14, as shown in FIG. 7 and FIGS. 12 to 14, the hook portion 81 with which the engagement pin 55 of the operation knob 13 is rotatably engaged is formed at the front end portion, while a connection pin 82 is formed at the rear end portion so that its opposite ends are projecting perpendicularly to the direction of movement. The opposite end portions of this connection pin 82 are fitted loosely to the long holes 73 made in the side plate portions 62 of the feed member 14. A long hole 83 extending in the direction of movement is formed between the hook portion 81 and the connection pin 82 in the connection member 15. A support pin 84 for engagement with the other end of the spring 16 is formed so as to extend in this long hole 83 in the direction perpendicularly to the direction of movement. The long hole 83 has a gentle slope 85 at the end on the connection pin 82 side, as shown in FIG. 12. Exaggerated in FIG. 7, the thickness of the hook portion 81 is set to be thick enough so that the hook portion 81 can be fitted into the opening 67 of the feed member 14.

Figure 15:
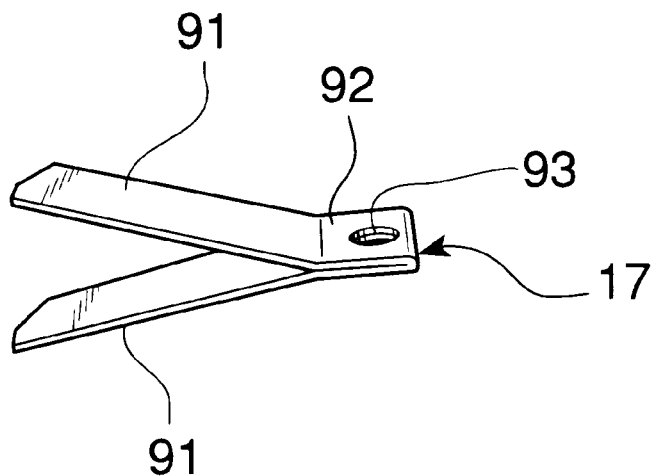
FIG. 15 is a perspective view illustrating a clip opening spring.

As shown in detail in FIG. 15, each of the pair of clip opening springs 17 is formed by bending a band-like elastic metal plate at its substantially central portion, and opening free ends 91 at the opposite ends, while closing the central portion as a top portion 92. Thus, each clip opening spring 17 has a substantially Y-shaped section. The top portion 92 is provided with an insertion hole 93 to be penetrated by the pin protrusion 30 erected in the bottom portion 22 of the lower casing 11.

Here, the attachment of the operation knob 13, the feed member 14 and so on to the upper casing 12 will be described. The operation knob 13 is inserted from its base portion 52 into the opening 34 of the upper casing 12. At this time, the operation knob 13 is inserted into the opening 34 in such a manner that the surface of the base portion 52 of the operation knob 13 is opposite to the upper side wall 31 of the upper casing 12, and the operation knob 13 is rotated by about 90 degrees when the front engagement portions 54 arrive at portions under the knob guide ribs 41 of the opening 34, so that the front engagement portions 54 are engaged with the base guide grooves 39 under the knob guide ribs 41. At this time, the rear engagement portions 56 of the operation knob 13 are put on the knob guide ribs 41. Therefore, when the operation knob 13 is moved back in this state, the rear engagement portions 56 are pushed down into the base guide grooves 39 through the insertion inlet 42 formed by the rear end portions of the knob guide ribs 41 and the front end portions of the restriction protrusions 43. Then, if the operation knob 13 is advanced, also the rear engagement portions 56 engages with the base guide grooves 39.

On the other hand, the feed member 14 is inserted into the opening 34 from the edge portion 64 at its rear end, so that the rear engagement protrusions 72 are put on the upper surfaces of the guide protrusions 49 while the projected pins 70 are disposed on the lower surface of the guide protrusions 49. Then, the front engagement protrusions 71 are put on the knob guide ribs 41. The opposite end portions of the connection pin 82 of the connection member 15 are fitted loosely into the opposite long holes 73 of the feed member 14. For this purpose, the connection pin 82 of the connection member 15 is disposed between the side plate portions 62 of the feed member 14, and the connection member 15 is rotated by about 90 degrees, so that the opposite end portions of the connection pin 82 can be put into the opposite long holes 73. Next, the spring 16 with its one end hooked on the engagement hook 44 is hooked on the support pin 84 of the connection member 15 at its other end, while the hook portion 81 of the connection member 15 is hooked on the engagement pin 55 of the operation knob 13.

The lower casing 11 is combined with the upper casing 12 to which the operation knob 13, the feed member 14 and so on have been attached thus. Before combining the lower casing 11 with the upper casing 12, the insertion holes 93 formed in the top portions 92 of the clip opening springs 17 are fitted onto the pin protrusions 30 of the lower casing 11 so that the pair of clip opening springs 17 are temporarily fixed to the bottom portion 22 of the lower casing 11. Then, a connection bar portion 98 formed in the form of a ring on the rear end of the upper casing 12 is fitted into a recess portion 97 formed in the form of a hook widthwise in the lower-rear-end portion of the lower casing 11. At the same time, the engagement protrusions 24 and the positioning protrusions 25 on the upper end surfaces of the opposite lower side walls 21 of the lower casing 11 are inserted into the engagement grooves 35 and the positioning holes 36 in the lower surfaces of the upper side walls 31, respectively. Finally, the front ends of the lower casing 11 and the upper casing 12 are combined by fitting a constriction band 96 made of a spring metal plate into a guide groove 95 formed so as to extend from the front-end-side outer circumferential surface of the lower casing 11 to the opposite side surfaces of the upper casing 12. Thus, the assembly is completed.

Next, the usage and operation of this clip driver 10 will be described with reference to FIG. 17 to FIG. 20.

Figure 17:
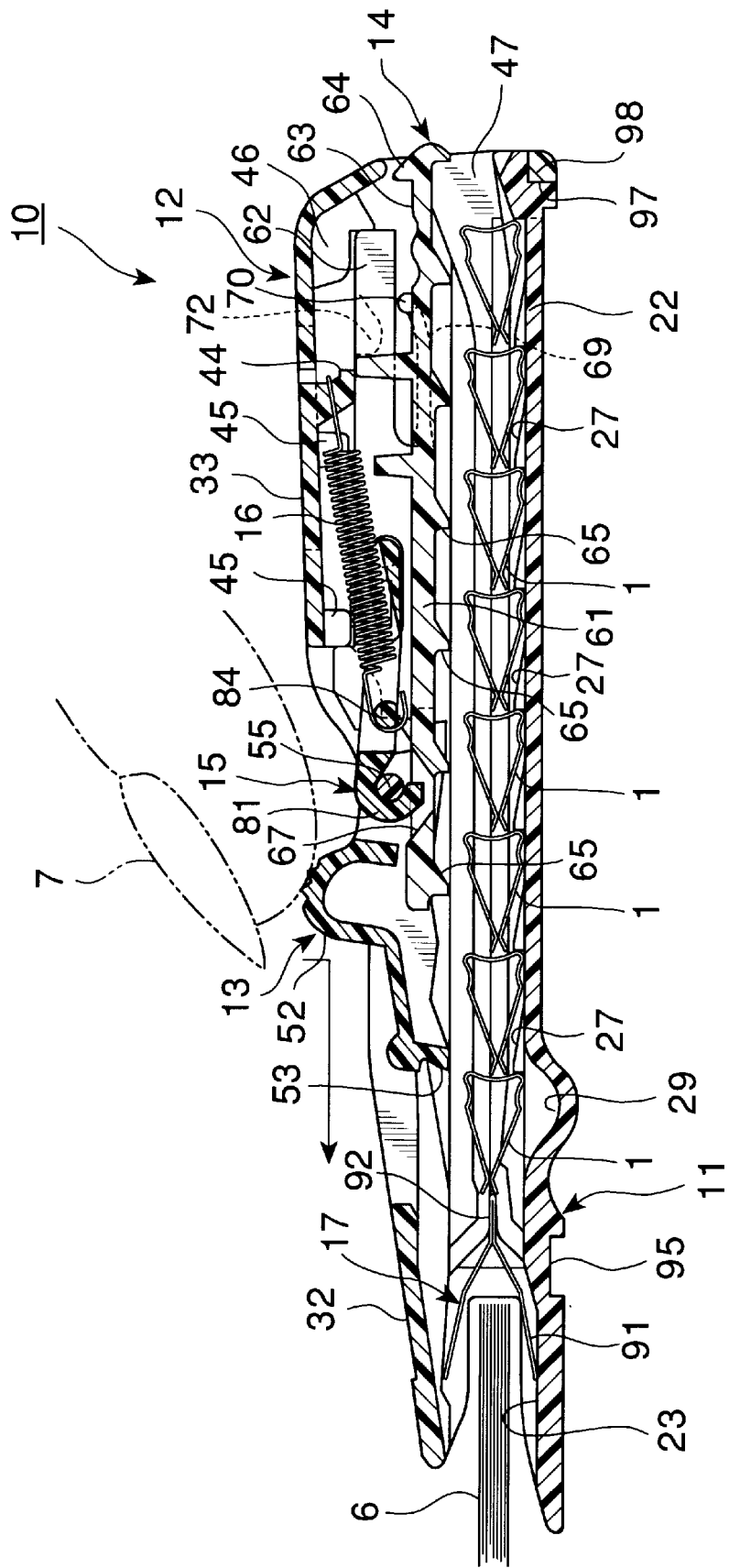
FIG. 17 is a longitudinally sectional side view for explaining the operation of the embodiment, showing a state in which the operation knob is not yet pushed down.

As shown in FIG. 17, the operation knob 13 and the feed member 14 are elastically drawn toward the rear end side by the spring 16 through the connection member 15. As a result, the obliquely upward inclined rear end surface of the operation knob 13 abuts against the front end portions 60 of the side plate portions 62 of the feed member 14 so that the front-end push-out portion 53 of the operation knob 13 is moved up. The moving-up of the front-end push-out portion 53 is kept in such a manner that it is restricted by the front engagement portions 54 which abut against the back surfaces of the knob guide ribs 41 of the opening 34 of the upper casing 12. On the other hand, the rear ends of the side plate portions 62 of the feed member 14 are restricted from going back by abutment against the pair of engagement protrusions 46, and the edge portion 64 at the rear end of the elastic portion 63 is slightly projecting from the clip insertion inlet 47. At this time, the front engagement protrusions 71 of the feed member 14 run on the upper surfaces of the restriction protrusions 43, and the rear engagement protrusions 72 get on the highest edges of the ascending slopes 50 of the guide protrusions 49. On the other hand, the upper ends of the side plate portions 62 of the feed member 14 engage with the hold protrusions 45 hanging down on the rear upper plate 33 so as to prevent the front end of the feed member 14 from being drawn up into a slanting state by the spring 16. Thus, the feed member 14 is kept substantially horizontal.

In this state, the clip 1 is charged from its guide portions 5 side through the clip insertion inlet 47. The clip insertion inlet 47 is made narrow by the edge portion 64 of the feed member 14. The edge portion 64 is now moved back by the spring 16. When the clip 1 is pushed in, the edge portion 64 is moved frontward, so that the opening of the clip insertion inlet 47 can be made wider. Thus, the clip 1 can be charged easily. The lug portions 4 of the charged clip 1 are fitted into the guide grooves formed by the combination of the lower lug-guide grooves 26 of the lower casing 11 and the upper lug-guide grooves 37 of the upper casing 12. When the clip insertion inlet 47 is turned up so that the front end of the clip driver 10 turns down, the charged clip 1 runs over the clip stopper protrusions 27 one after another successively as if it climbs the gentle slopes of the clip stopper protrusions 27 formed on the bottom portion 22 of the lower casing 11. The clip 1 slides toward the front end portion. Arriving at the front end portion, the clip 1 stops when the top portions 92 of the clip opening springs 17 are inserted between the lug portions 4 at the opposite ends of the closed guide portions 15, respectively. The back portion 2 of the clip 1 at the head faces the vertical surfaces of the clip stopper protrusions 27 located in the front.

The guide portions 5 of the next or second charged clip 1 abut against the back portion 2 of the clip 1 at the head. Then, the back portion 2 of the second charged clip 1 is opposite to the vertical surfaces of the second clip stopper protrusions 27. In this embodiment, eight clips 1 can be charged in the same manner. If the front end of the clip driver 10 is turned up so that the clips insertion inlet 47 is turned down, there is no fear that these clip 1 move back to the rear end side, because the back portions 2 of the clips 1 abut against the vertical surfaces of the clip stopper protrusions 27 opposite thereto, respectively. When the clip driver 10 is turned upside down so that the lower casing 11 comes on the upper side and the upper casing 12 comes on the lower side, the clips 1 will not be restricted by the clip stopper protrusions 27, and in addition, since the feed member 14 is also lifted up, the clips 1 can move forward and backward desirably without restriction by the clip feed protrusions 65. However, there is no fear that the clips 1 lie on top of one another, because the lug portions 4 of the respective clips 1 are fitted into the guide grooves for guiding the lug portions.

Here, after the documents 6 to be clipped are inserted into the paper insertion inlet 18 of the clip driver 10, a finger 7 is put on the knob protrusion 52 of the operation knob 13, so as to push and slide the knob protrusion 52 toward the front end as shown in the arrow. The push-out portion 53 which is now biased up by the spring 16 is moved down by the downward pressure of the knob protrusion 52. This moving-down of the push-out portion 53 is restricted by the fact that the engagement protrusions 57 on the lower surfaces of the opposite ends of the knob protrusion 52 abut against the upper surfaces of the knob guide ribs 41 of the opening 34. At first only the operation knob 13 advances as the knob protrusion 52 is slid toward the front end. This is because the connection pin 82 of the connection member 15 is loosely fitted in the long holes 73 of the feed member 14 so that only the operation knob 13 advances till the front end of the hook portion 81 of the connection member 15 abuts against the slope on the front end of the opening 67 of the connection member 15. When the front end of the hook portion 81 abuts against the slope on the front end of the opening 67 of the connection member 15, the advance of the operation knob 13 makes the feed member 14 advance through the connection member 15.

When the feed member 14 is slid toward the front end, the feed member 14 is released from the state where the front engagement protrusions 71 are put on the upper surfaces of the restriction protrusions 43 and the rear engagement protrusions 72 are put on the edges of the ascending slopes 50 of the guide protrusions 49, so that the feed member 14 moves down substantially horizontally. As a result, the front engagement protrusions 71 abut against the upper surfaces of the knob guide ribs 41, while the rear engagement protrusions 72 and the protrusion pins 70 are disposed to hold therebetween the guide protrusions 49 located at the same height as the knob guide ribs 41.

Figure 18:
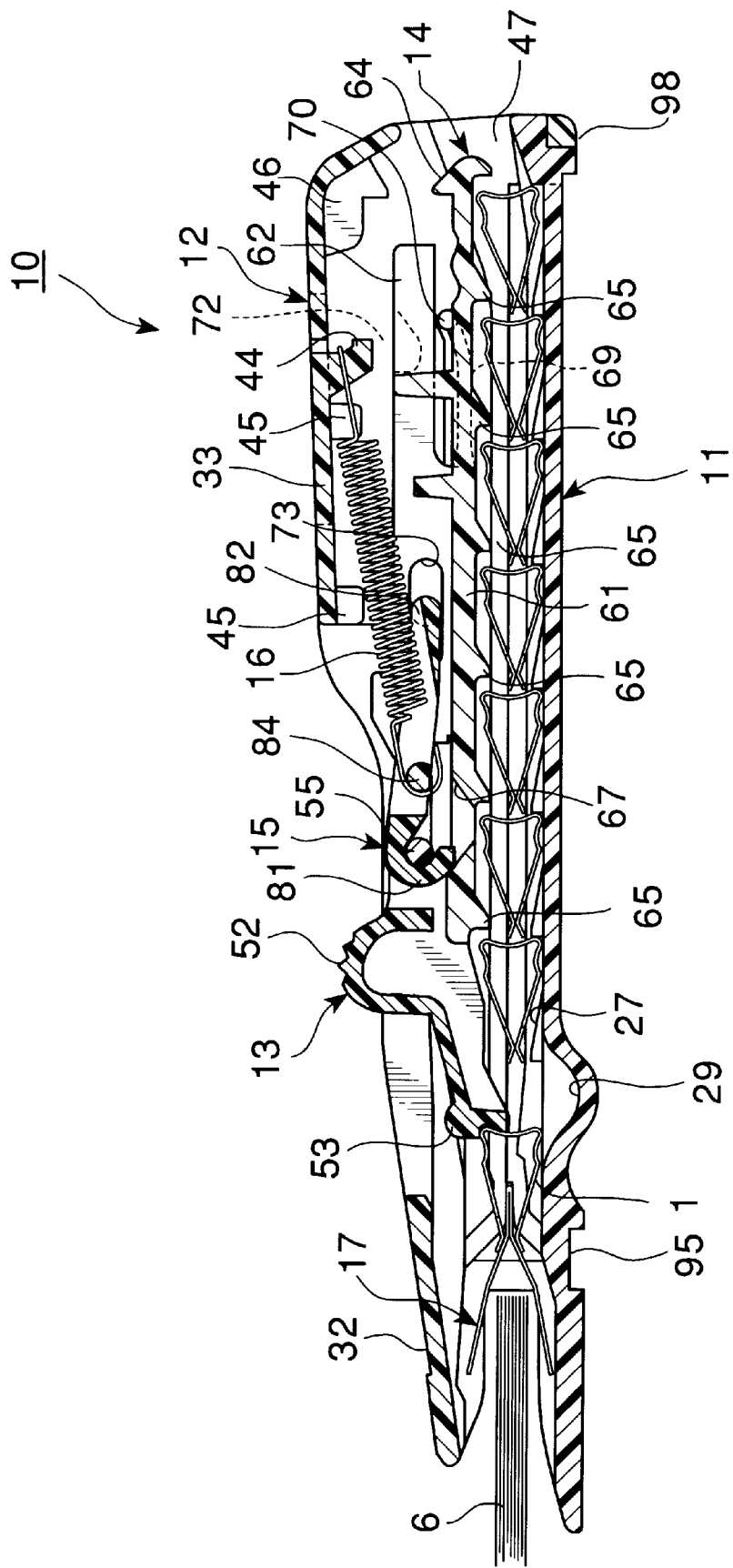
FIG. 18 is a longitudinally sectional side view for explaining the operation of the embodiment, showing a state in which the operation knob has been pushed down.

As shown in FIG. 18, the vertical surfaces of the clip feed protrusions 65 formed on the back of the base portion 61 of the feed member 14 can abut against the back portions 2 of the second clip 1 and the followings when the front engagement protrusions 71 and the rear engagement protrusions 72 of the feed member 14 abut against the upper surfaces of the knob guide ribs 41 and the guide protrusions 49, respectively. In addition, with the feed member 14 moving down, the position of the connection pin 82 of the connection member 15 also moves down. As a result, the connection member 15 moves up slightly on the hook portion 81 side. Consequently, the hook portion 81 which is in contact with the front-end slope of the opening 67 to block the advance can go over the front-end slope of the opening 67. The connection member 15 advances together with the operation knob 13 till the connection pin 82 of the connection member 15 abuts against the front end portions of the long holes 73 of the feed member 14, while the feed member 14 is stopping in its lowered position. Thus, only the operation knob 13 is advanced at first. This is because the distance from the point where the top portions 92 of the clip opening springs 17 come into contact with the frontmost clip 1 between the lug portions 4 thereof to the point where the clip 1 is passed through the clip opening springs 17 so as to be discharged to the paper insertion inlet 18, is longer than the distance from the front ends of the guide portions 5 of the clip 1 to the back portion 2 thereof Therefore, only the operation knob 13 is advanced by the difference between the above-mentioned two distances at first, and then, the feed member 14 is moved forward in such a manner as will described below.

Figure 19:
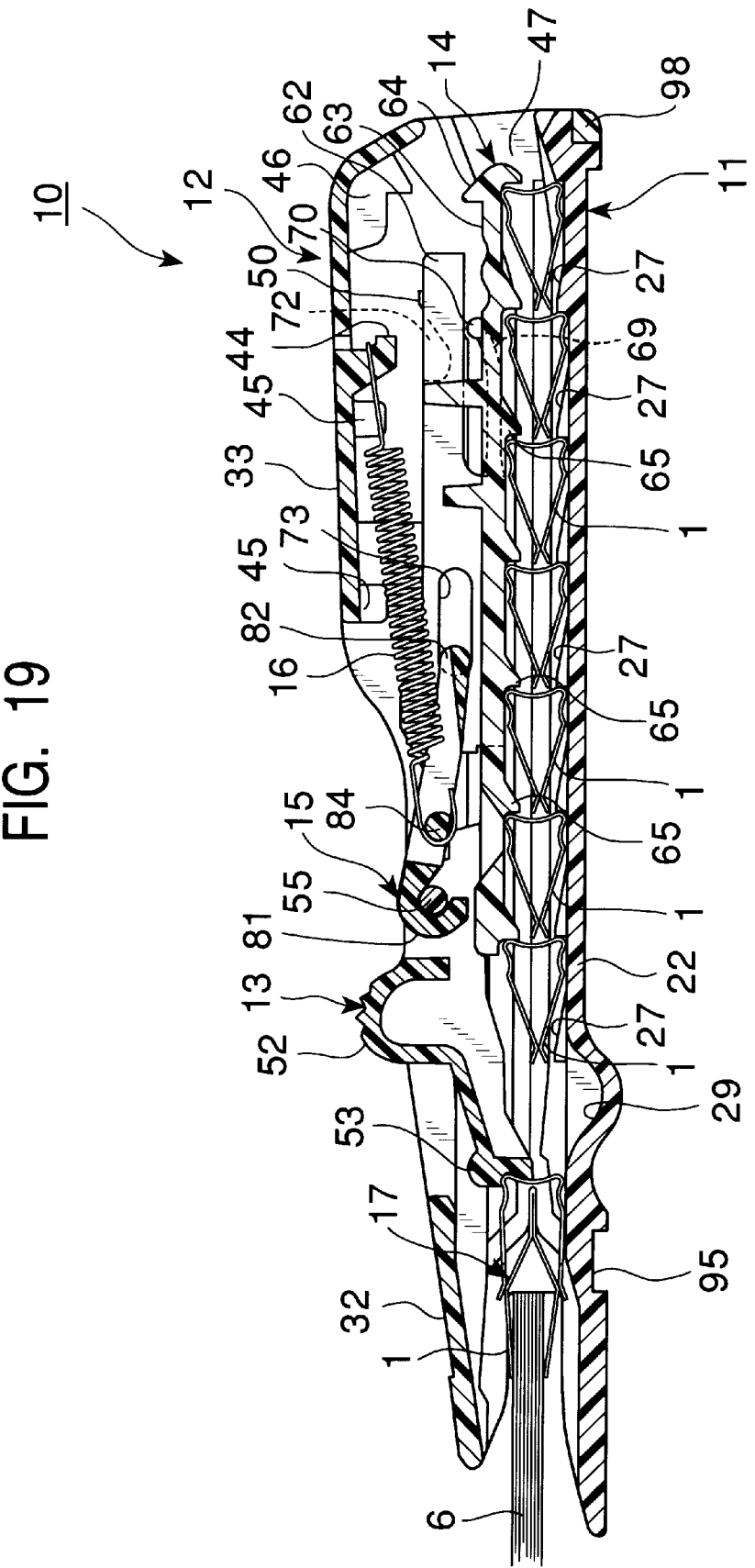
FIG. 19 is a longitudinally sectional side view for explaining the operation in the embodiment, showing a state in which the operation knob has been advanced from FIG. 18.

By the operation knob 13 advanced together with the connection member 15, the lug portions 4 of the frontmost clip 1 enter into the top portions of the clip opening springs 17. When the operation knob 13 is further moved forward, the clip 1 moves forward, and the two abutment portions 3 of the clip 1 are spread by the clip opening springs 17, as shown in FIG. 19. When the front end of the clip 1 reaches the paper insertion inlet 18, the two abutment portions 3 are opened to be substantially parallel, so that the documents 6 can be inserted therebetween. At this time, the connection pin 82 of the connection member 15 is located in the front end portions of the long holes 73 of the feed member 14. Thereafter, therefore, the feed member 14 will also move forward with the advance of the operation knob 13.

Figure 20:
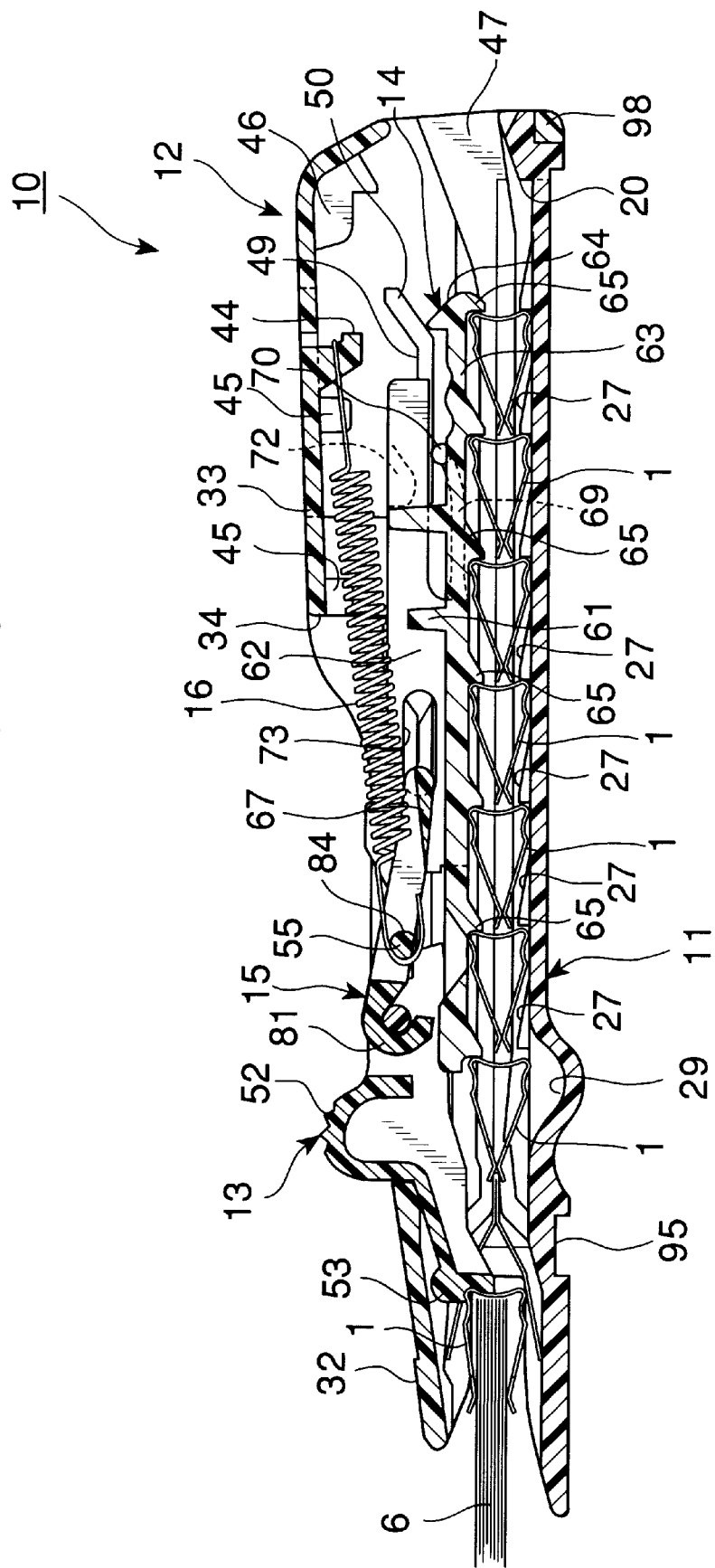
FIG. 20 is a longitudinally sectional side view for explaining the operation in the embodiment, showing a state in which the operation knob has been advanced to the maximum.

When the operation knob 13 is further moved forward, the engagement between the clip opening springs 17 and the lug portions 4 of the clip 1 is released, so that the clip 1 which is now binding the documents 6 can be discharged from the paper insertion inlet 18. On the other hand, in the feed member 14 which is advanced as the operation knob 13 advances, the clip feed protrusions 65 formed on the back of the base portion 61 abut against the corner portions of the second clip 1 and the followings so that those clips 1 are advanced while climbing the slopes of the clip stopper protrusions 27 formed on the upper surface of the bottom portion 22 of the casing 11 and located in front of the clips 1. As shown in FIG. 20, when the border portion between the base portion 51 and the knob protrusions 52 of the operation knob 13 abuts against the front end portion of the opening 34 so as to prevent the operation knob 13 from advancing more, the operation knob 13 makes the clip 1 with the documents 6 clipped part from the clip opening springs 17 completely. Then, the second clip 1 comes at the head, and the third clip 1 is engaged with the second clip stopper protrusions 27. The fourth clip 1 and the followings are also engaged with the clip stopper protrusions 27 which are located just in front of those with which the fourth clip 1 and the followings were engaged, respectively.

When the documents 6 clipped with the clip 1 is taken out, and the finger 7 is separated from the operation knob 13, the operation knob 13 and the feed member 14 are pulled back toward the rear end by the spring 16. The feed member 14 is moved back in its lowered state till the front engagement protrusions 71 run on the restriction protrusions 43 formed on the upper side walls 31 of the upper casing 12. Therefore, the clip feed protrusions 65 of the feed member 14 abut the bent portions of the second clip 1 and the followings. However, since the respective clip feed protrusions 65 are inclined rearwardly, the feed member 14 can run over the bent portions of the clips 1 and further move back even if the feed member 14 hits on the bent portions. Since the bent portions located in the lower portions of the respective clips 1 abut against the vertical surfaces of the clip stopper protrusions 27 formed on the bottom portion 22 of the lower casing 11, there is no fear that the clips 1 move back by the force in running over the clip feed protrusions 65. The feed member 14 thus moved back rise's such that the front engagement protrusions 71 run on the restriction protrusions 43 while the rear, engagement protrusions 72 run on the front ends of the ascending slopes 50. The moving-back of the feed member 14 ceases when the rear ends of the side plate portions 62 are engaged with the engagement protrusions 46. On the other hand, the rear end of the base portion 51 of the operation knob 13 abuts against the front end portions 60 of the side plate portions 62 of the feed member 14. Thus, the operation knob 13 also returns to its initial state shown in FIG. 17, where the push-out portion 53 is lifted up.

When the operation knob 13 and the feed member 14 return thus, the clip 1 which has been located in the second position is now disposed at the head, and the respective following clips 1 are also advanced successively. Therefore, even if the front end of the clip driver 10 is turned up, the next clip 1 can be positioned adjacent to the clip opening springs 17, so that it is possible to perform continuous clipping.

In the above-mentioned embodiment, the engagement protrusions 24 and the positioning protrusions 25 are formed on the upper end surfaces of the opposite lower side walls 21 of the lower casing 11, while the engagement grooves 35 and the positioning holes 36 are formed in the lower end surface of the upper casing 12. Then, the engagement protrusions 24 and the positioning protrusions 25 are inserted into the engagement grooves 35 and the positioning holes 36 respectively to thereby combine the lower casing 11 and the upper casing 12. The alignment of the lower casing 11 and the upper casing 12 can be carried out satisfactorily only by fitting the connection bar portion 98 of the upper casing 12 into the recess portion 97 of the lower casing 11. Therefore, it is not always necessary to provide the engagement protrusions 24, the positioning protrusions 25, the engagement grooves 35 and the positioning holes 36. In addition, the upper end surfaces of the opposite lower side walls 21 of the lower casing 11 and the lower end surface of the upper casing 12 may be joined by bonding or heat thermal welding. In this case, the guide groove 95 and the constriction band 96 also become unnecessary.

Figure 5:
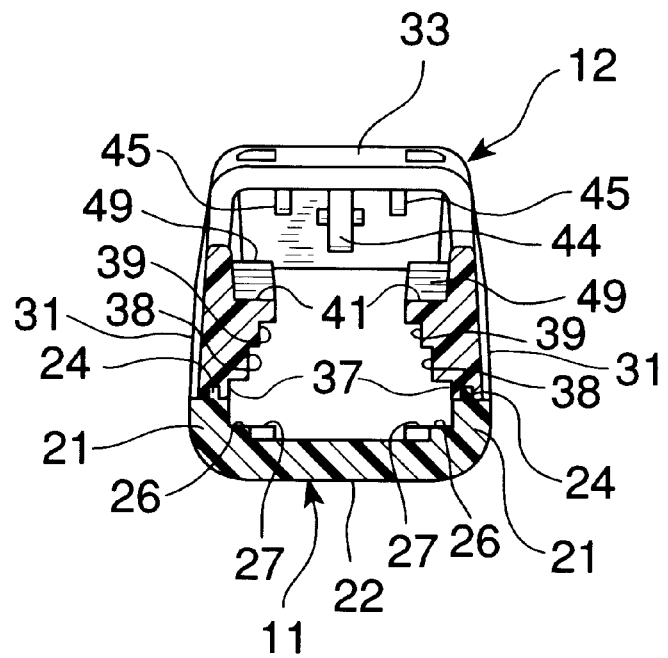
FIG. 5 is a longitudinally sectional view taken on line V—V of FIG. 4.
Figure 6:
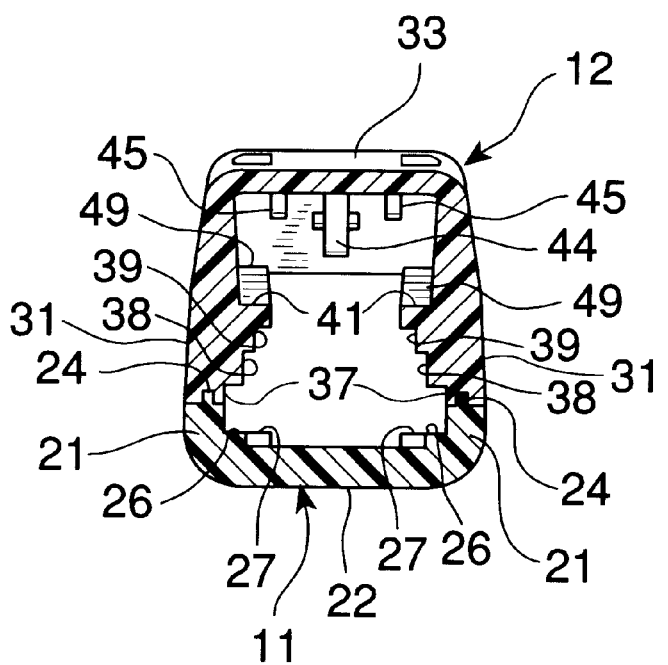
FIG. 6 is a longitudinally sectional view taken on line VI—VI of FIG. 4.
Figure 7:
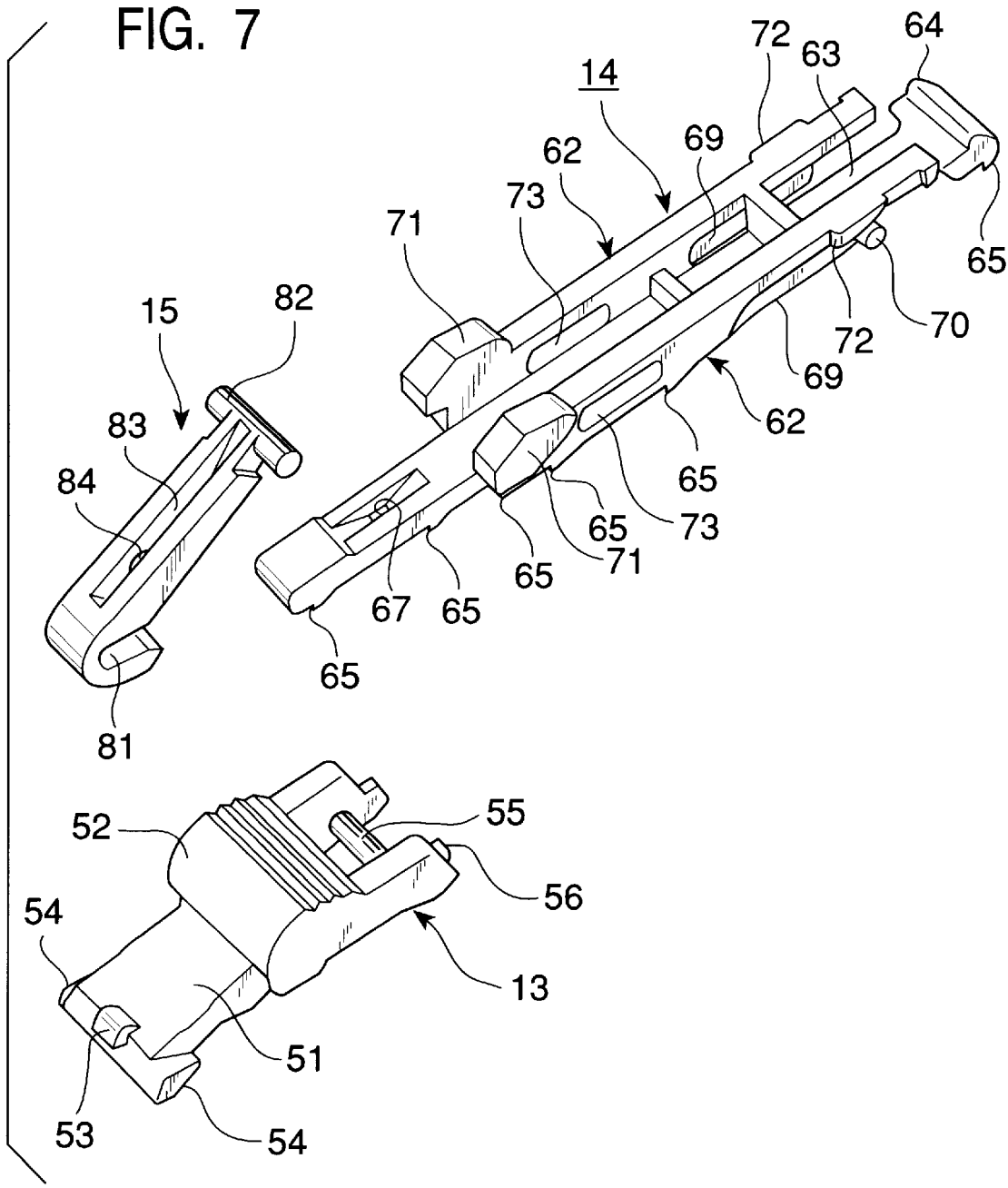
FIG. 7 is an exploded perspective view illustrating only an operation knob, a feed member and a connection member for connecting the former two in the embodiment.
Figure 8:
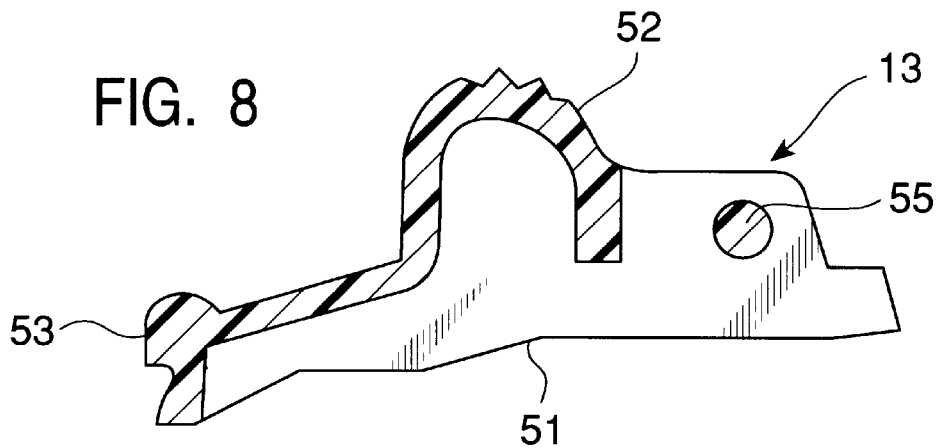
FIG. 8 is a longitudinally sectional view of the operation knob in FIG. 7.
Figure 9:
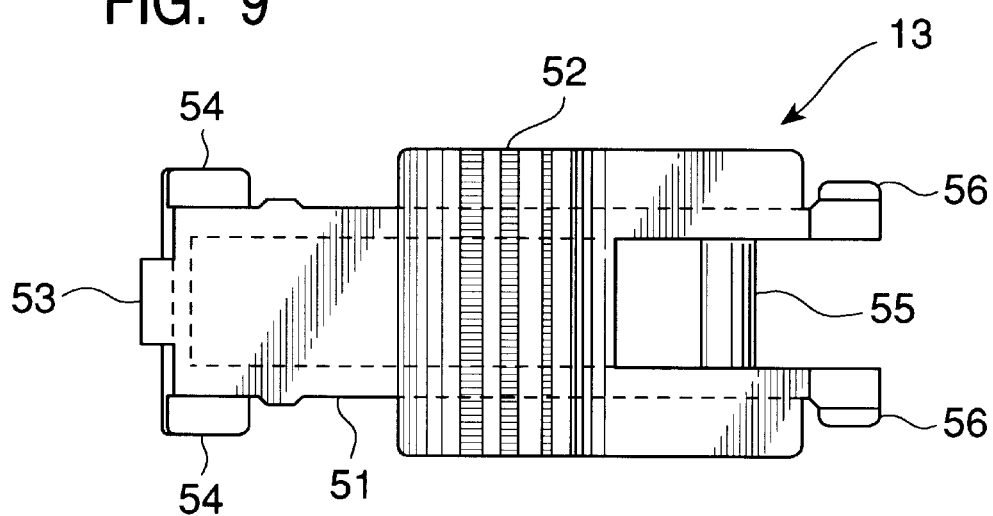
FIG. 9 is a plan view of the operation knob in FIG. 7.
Figure 10:
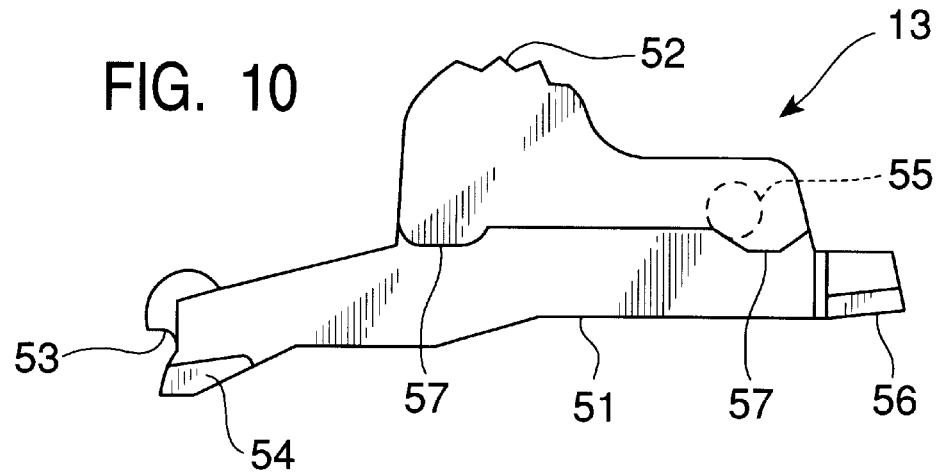
FIG. 10 is a side view of the operation knob in FIG. 7.
Figure 11:
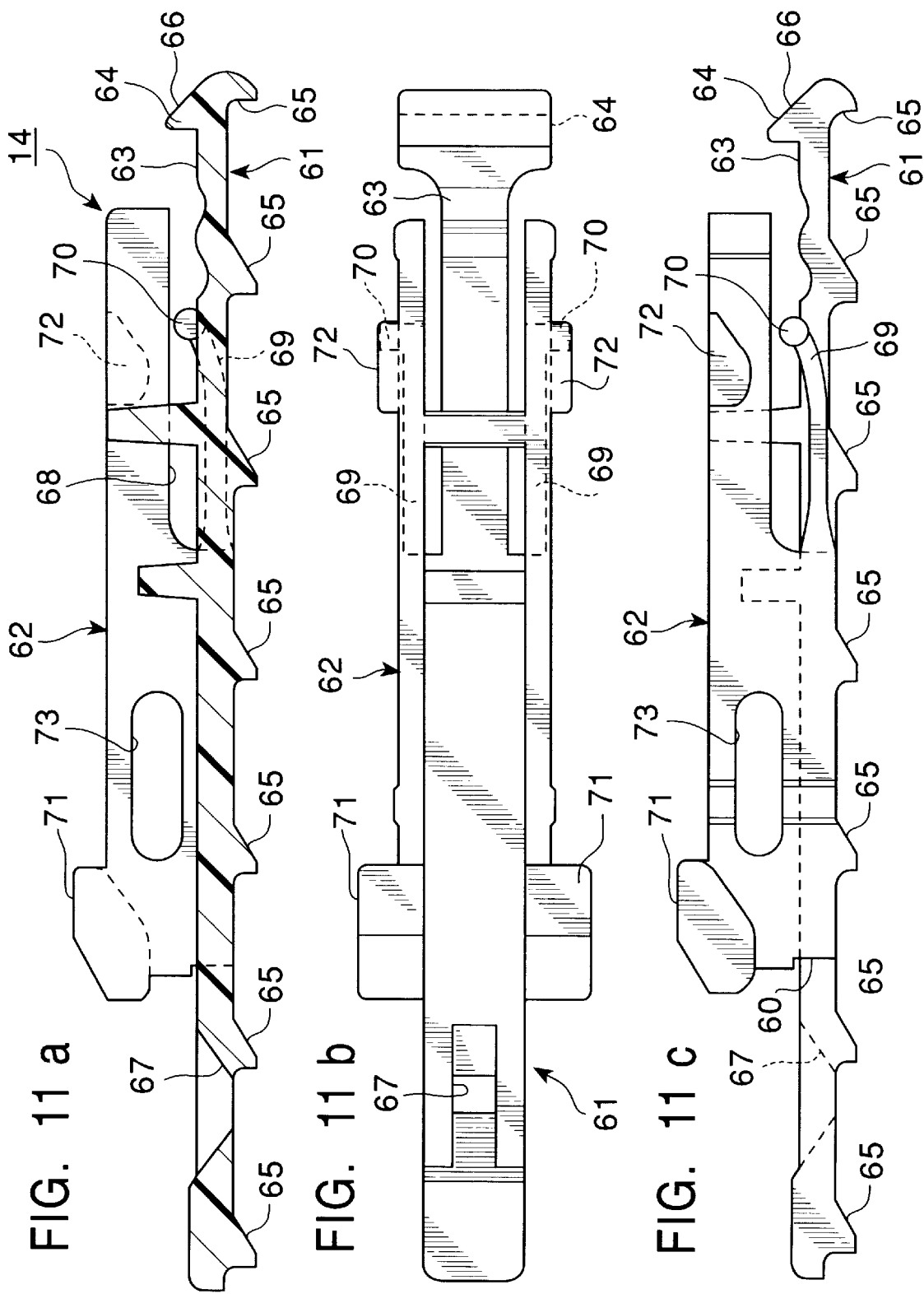
FIG. 11a is a longitudinally sectional view illustrating the feed member in FIG. 7.
FIG. 11b is a plan view of the same feed member.
FIG. 11c is a side view of the same feed member.

Further, although the casing body is divided horizontally into the lower casing 11 and the upper casing 12 in the above-mentioned embodiment, the casing body may be divided vertically, that is, cut substantially at the center vertically in FIGS. 5 and 6 so that the casing body is constituted by a left casing portion and a right casing portion. In this case, preferably, the two casing portions are combined in such a manner that the front engagement portions 54, the rear engagement portions 56, the protrusion pins 70, the front engagement protrusions 71, and so on formed on the one-side surface of the operation knob 13, the feed member 14, and so on, are engaged with the base guide grooves 39 and the knob guide ribs 41 of the right or left casing portions, while the front engagement portions 54 and so on formed in the same manner on the other-side surfaces of the operation knob 13, the feed member 14, and so on are engaged with the base guide grooves 39 and the knob guide ribs 41 of the left or right casing portions.

As has been described, according to the feature of the invention, the continuous operation of the clip driver is made possible by such a simple structure that a feed member which is longitudinally movable together with the longitudinal movement of the operation knob is provided in the casing body, and a plurality of feed protrusions is provided on the feed member so that the feed protrusions make a second clip and the followings advance simultaneously when the feed member advances, while the feed member can retreat without making the advanced clips retreat by the feed protrusions. Further, since the clip insertion inlet is provided in the rear end of the casing body, the clips can be charged very simply.

According to the feature of the invention, since only the operation knob can be advanced by a predetermined distance, passing over the distance required for a clip to pass by the clip opening springs having a length longer than the length of the clip in the advancing direction, can be carried out by making the operation knob advance by the distance equivalent to the difference between the length of the clip opening springs and the length of the clip, so that the document clipping operation and the successive feeding of the second clip and the followings can be carried out surely.

According to the feature of the invention, the movement of only the operation knob can be made possible by such a simple structure that the rear end portion of the connection member is loosely fitted into a long hole extending longitudinally in the feed member.

According to the feature of the invention, since the feed member is held in a higher position when it is retreated, the rear end of the feed member is located in the upper portion of the clip insertion inlet so that the inserted clip is prevented from falling out of the clip insertion inlet, while when a clip is to be inserted into the it clip insertion inlet, the feed member is made to advance by the clip to be inserted so as to allow insertion of the clip easily.

According to the feature of the invention, the feed member can be held in a higher position when the feed member is retreated, by such a simple structure that the engagement protrusions of the feed member are mounted on the restriction/guide protrusions which are disposed on the rear portions inside the casing body at an interval in the longitudinal direction on each of widthwise opposite side portions of the casing body so that each of the restriction/guide protrusions extends to ascend up toward the rear end side of the casing body.

According to the feature of the invention, the feed member is held substantially horizontally not only in the case where the feed member retreats but also in the case where the feed member descends and advances. Accordingly, when the feed member feeds the second clip and the followings, the feed member can makes these clips advance surely, while when the feed member is in the retreated state, the feed member does not prevent movement of clips to be charged.

According to the feature of the invention, each clip can get over the front-side clip stopper means because of presence of the slanting surface of the clip stopper means and this clip is prevented by the vertical surface of the clip stopper means from retreating after this clip has gone over the clip stopper means. On the other hand, when the feed member advances, the second clip and the followings are fed forward by the respective vertical surfaces of the feed protrusions, while when the feed member retreats, the feed protrusions can get over the clips with their slanting surfaces without making the clips retreat. According to the feature of the invention, the connection member can be formed with a simple structure so that it can be made small in size.

According to the feature of the invention, since the interval between the clip stopper protrusions is substantially equal to the length of each clip from the back portion to the forward end of the abutment portions, only one clip is disposed between adjacent two clip stopper protrusions so that the clips can be prevented from piling up.

According to the feature of the invention, strong elastic force is generated in the elastic members by the elastic arms so that the feed member can be surely held by the restriction/guide protrusions.

What is claimed is:

1. A clip driver for driving a plurality of clips one by one, each of said clips being formed by a back portion and abutment portions abutting against each other elastically, said clip driver comprising:

a casing body for accommodating said plurality of clips, said casing body including a sheet-like member insertion inlet formed at a front end of said casing body for inserting sheet-like members to be clipped, a clip insertion inlet formed at a rear end of said casing body for inserting said clips one by one, an opening formed in a front end upper surface of said casing body so as to extend in a longitudinal direction of said casing body, a clip path formed in said casing body so as to extend from said sheet-like member insertion inlet to said clip insertion inlet, and clip stopper means for engagement with said clips so as to allow said clips to advance but prevent said clips from retreating;

clip opening springs disposed in said casing body in a vicinity of said sheet-like member insertion inlet of said casing body for opening a nip between said abutment portions of a frontmost clip;

an operation knob fitted into said opening so as to be movable in the longitudinal direction of said casing body for feeding the frontmost clip in said clip path toward said sheet-like member insertion inlet over said clip opening springs by means of a front end of said operation knob;

a feed member which is movable together with movement of said operation knob in the longitudinal direction of said casing body, said feed member having a plurality of feed protrusions which make a second and following clips advance simultaneously when said feed member advances, while said feed member can retreat without making said advanced clips retreat by said feed protrusions; and elastic means for always elastically biasing said operation knob and said feed member toward the rear end of said casing body.

2. A clip driver according to claim 1, further comprising a connection member for connecting said operation knob and said feed member so that said feed member advances after only said operation knob advances by a predetermined distance to feed said frontmost clip forward.

3. A clip driver according to claim 1, further comprising a connection member connected to said feed member in such a manner that one end of said connection member is connected to said operation knob and the other end of said connection member is connected to said feed member in a manner so that said other end is loosely fitted into a long hole which is formed in said feed member so as to extend in a longitudinal direction of said feed member, whereby said feed member advances after only said operation knob advances by a predetermined distance to feed said frontmost clip forward.

4. A clip driver according to claim 1, wherein said casing body includes restriction/guide protrusions which are formed so as to keep said feed member in a first position when said feed member advances and in a second position higher than said first position when said feed member retreats, whereby a rear end of said feed member is located above said clip insertion inlet so that, when a clip is to be inserted into said clip insertion inlet, said feed member is moved forward by the clip to be inserted so as to allow insertion of the clip, while the thus inserted clip is prevented from falling out of said clip insertion inlet by the rear end of said feed member.

5. A clip driver according to claim 1, wherein said casing body includes restriction/guide protrusions which are formed at a rear portion inside said casing body for keeping said feed member in a first position when said feed member advances and in a second position higher than said first position when said feed members retreats, said restriction/guide protrusions being disposed at an interval in the longitudinal direction on widthwise opposite side portions of said casing body, and wherein said feed member includes engagement protrusions which are formed at an interval in the longitudinal direction on widthwise opposite side surfaces in front and rear end portions of said feed member so that when said feed member is made to retreat, said feed member retreats in a state that said engagement protrusions are mounted on said restriction/guide protrusions.

6. A clip driver according to claim 1, wherein said casing body includes restriction/guide protrusions which are formed at a rear portion inside said casing body so as to be disposed at an interval in the longitudinal direction on widthwise opposite side portions of said casing body; wherein in each pair of said restriction/guide protrusions disposed at front and rear positions in the longitudinal direction, each of the restriction/guide protrusions located at the rear portions is constituted by a horizontal portions extending substantially horizontally from a front end to a rear end thereof and a slanting portion extending upward from the rear end of said horizontal portion toward the rear end of said casing body; wherein said casing body further includes ribs which are formed on widthwise opposite side portions of said opening of said casing body so as to slightly project toward said opening and extend longitudinally in a height substantially identical with the height of said horizontal portions of the rear-side restriction/guide protrusions; and wherein said feed member includes engagement protrusions which are disposed at an interval on longitudinally front and rear ends of widthwise opposite sides of said feed member so that, when said feed member is made to retreat, said feed member retreats in a state that said engagement protrusions are mounted on said restriction/guide protrusions, and said feed member further includes elastic members formed on widthwise opposite sides at a rear end lower portion of said feed member so that said elastic members engage with lower surfaces of the rear-side restriction/guide protrusions, whereby when said feed member advances, the front-side engagement protrusions of said feed member are mounted on said ribs while the rear-side engagement protrusions and said elastic members sandwich said horizontal portions therebetween so that said feed member can advance substantially horizontally.

7. A clip driver according to claim 6, wherein each of said elastic members is constituted by an elastic arm having an end fixed on a side lower surface of said feed member and being extended upward, and a projected pin formed at a free end of said elastic arm so as to be able to slidably contact with the lower surface of the rear-side restriction/guide protrusion.

8. A clip driver according to claim 1, wherein each of said clip stopper means and said feed protrusions has a rear end constituted by a slanting surface and a front end constituted by a substantially vertical surface.

9. A clip driver according to claim 1, further comprising a connection member one end of which is longitudinally movably connected to said feed member while the other end of which is rotatably connected to said operation knob, so that said feed member advances after only said operation knob advances by a predetermined distance to feed said frontmost clip forward.

10. A clip driver according to claim 1, wherein said clip stopper means includes a plurality of clip stopper protrusions formed at intervals each of which is substantially equal to a length of each clip from said back portion to the forward ends of said abutment portions.

* * * * *